(12) United States Patent
Cherif Cheikh

(10) Patent No.: US 7,815,928 B2
(45) Date of Patent: Oct. 19, 2010

(54) DEVICE FOR LOCAL ADMINISTRATION OF SOLID OR SEMI-SOLID FORMULATIONS AND DELAYED-RELEASE FORMULATIONS FOR PROPOSAL PARENTERAL ADMINISTRATION AND PREPARATION PROCESS

(75) Inventor: Roland Cherif Cheikh, Issy les Moulineaux (FR)

(73) Assignee: Societe de Conseils de Recherches et d'Applications Scientifiques SCRAS, Paris (FR)

(*) Notice: Subject to any disclaimer, the term of this patent is extended or adjusted under 35 U.S.C. 154(b) by 0 days.

(21) Appl. No.: 11/840,271

(22) Filed: Aug. 17, 2007

(65) Prior Publication Data
US 2007/0292473 A1 Dec. 20, 2007

Related U.S. Application Data

(60) Division of application No. 10/060,146, filed on Feb. 1, 2002, now abandoned, which is a continuation of application No. 09/319,159, filed as application No. PCT/FR97/02182 on Dec. 2, 1997, now abandoned.

(30) Foreign Application Priority Data
Dec. 2, 1996 (FR) .................................. 96 14755

(51) Int. Cl.
    *A61F 2/00* (2006.01)
(52) U.S. Cl. ...................................... 424/426; 424/423
(58) Field of Classification Search .................. 424/426
    See application file for complete search history.

(56) References Cited

U.S. PATENT DOCUMENTS

| | | | |
|---|---|---|---|
| 3,773,919 A | 11/1973 | Boswell et al. | |
| 4,675,189 A | 6/1987 | Kent et al. | |
| 5,242,910 A | 9/1993 | Damanj | |
| 5,366,734 A | 11/1994 | Hutchinson | |
| 5,445,832 A | 8/1995 | Orsolini et al. | |
| 5,492,697 A | 2/1996 | Boyan et al. | |
| 5,543,156 A | 8/1996 | Roorda et al. | |
| 5,573,542 A | 11/1996 | Stevens | |
| 6,120,786 A * | 9/2000 | Cherif Cheikh | 424/426 |

FOREIGN PATENT DOCUMENTS

| | | |
|---|---|---|
| DE | 522 404 | 3/1991 |
| EP | 0 134 318 | 3/1985 |
| EP | 0 257 369 | 3/1988 |
| EP | 0 283 458 | 9/1988 |
| EP | 0283458 A2 | 9/1988 |
| EP | 0 529 675 | 3/1993 |
| EP | 0 596 161 | 5/1994 |
| GB | 2 091 554 | 8/1982 |
| NZ | 199732 | 8/1985 |
| NZ | 236113 | 5/1993 |
| NZ | 223469 | 3/1994 |
| WO | 84/00304 | 2/1984 |
| WO | WO 84/00304 * | 2/1984 |
| WO | WO 85/03227 | 8/1985 |
| WO | WO 96/08289 * | 3/1996 |
| WO | WO 98/09613 A1 | 3/1998 |

* cited by examiner

*Primary Examiner*—Jake M. Vu
(74) *Attorney, Agent, or Firm*—Young & Thompson

(57) ABSTRACT

A method for implanting or inserting a solid or semisolid formulation containing at least one active principle uses a device comprising one part set inside the body of the patient and which conditions the solid or semisolid form, brings these conditioning action to the deposit site, injects or inserts in this deposit site, and withdraws after injection or insertion, with one part remaining outside and activating the functions of the device. The invention also concerns a sustained-release solid formulation for parenteral administration comprising a homogeneous mixture of an active principle in non-dispersed state and of a biologically compatible and biodegradable excipient, in which the amount of active principle is at least 50% by weight.

48 Claims, 21 Drawing Sheets

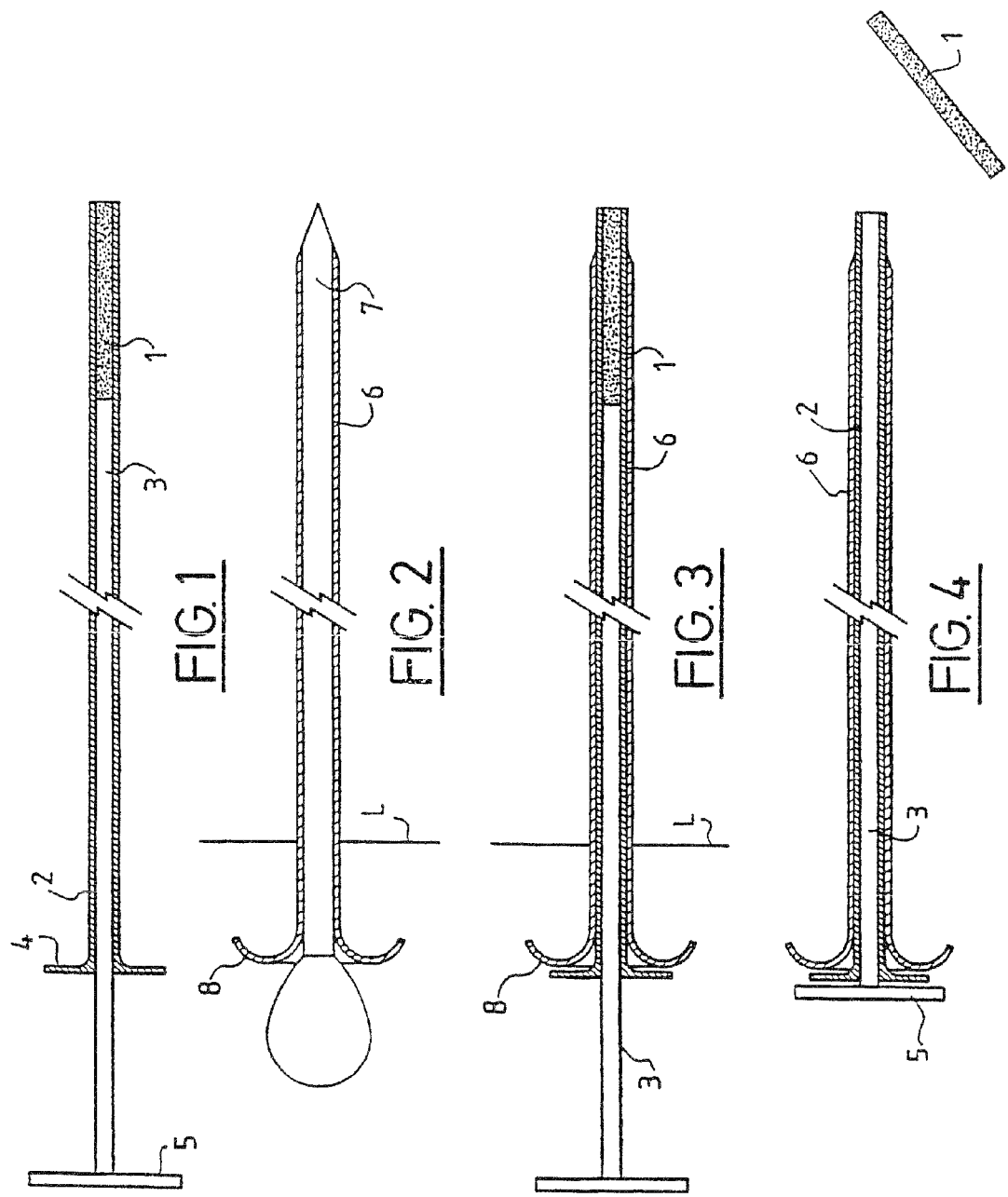

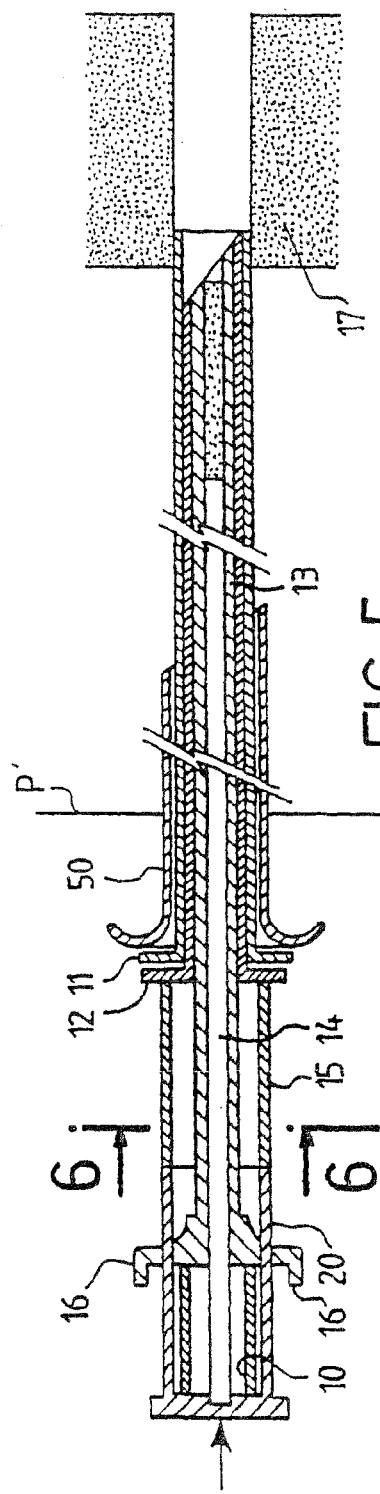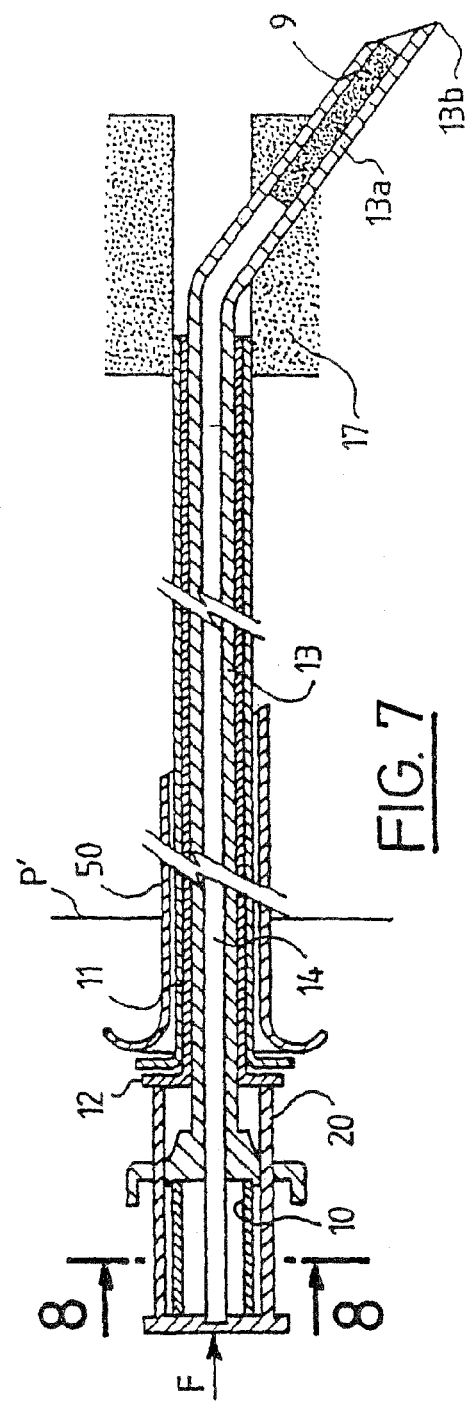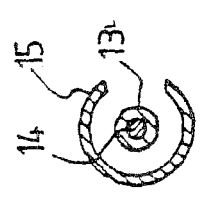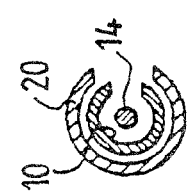

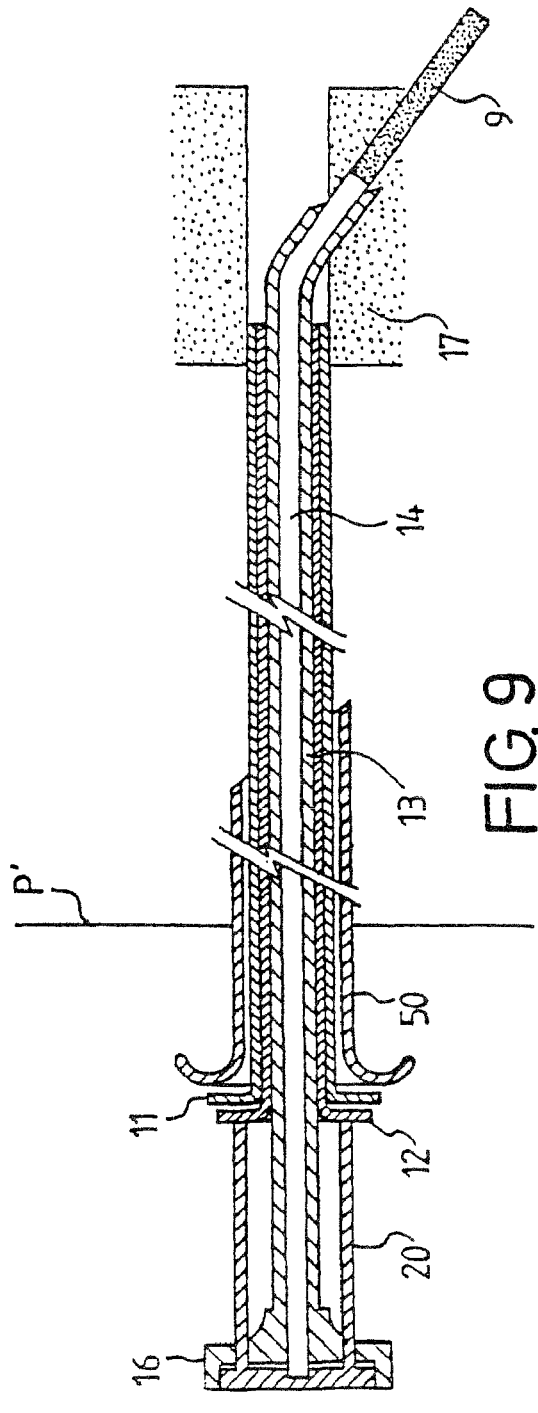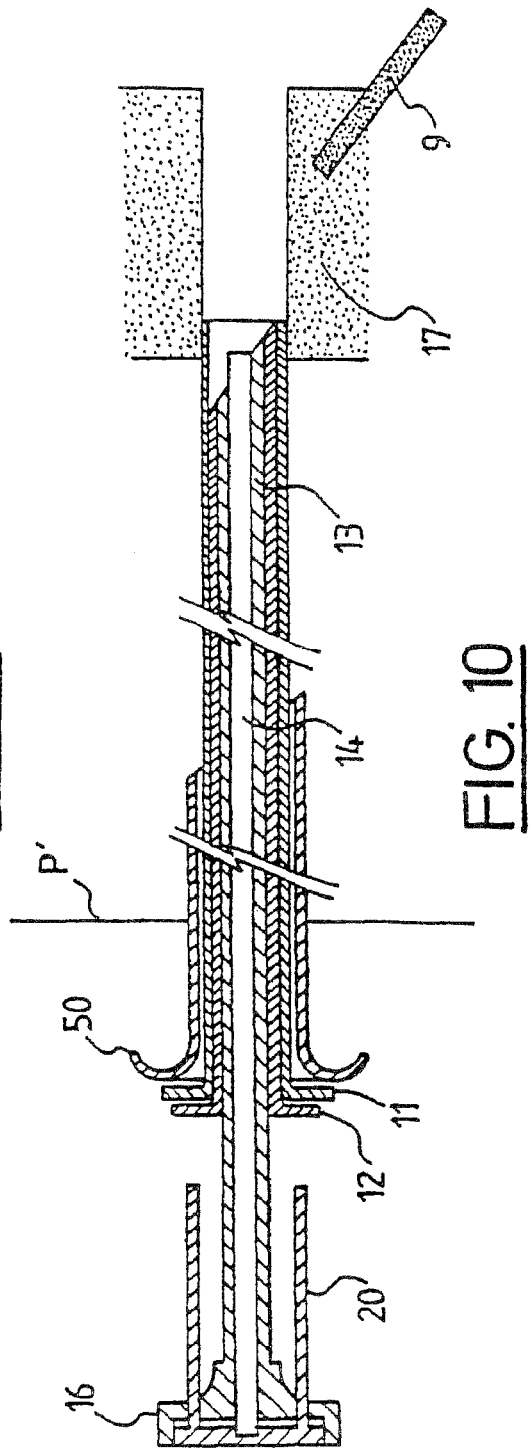

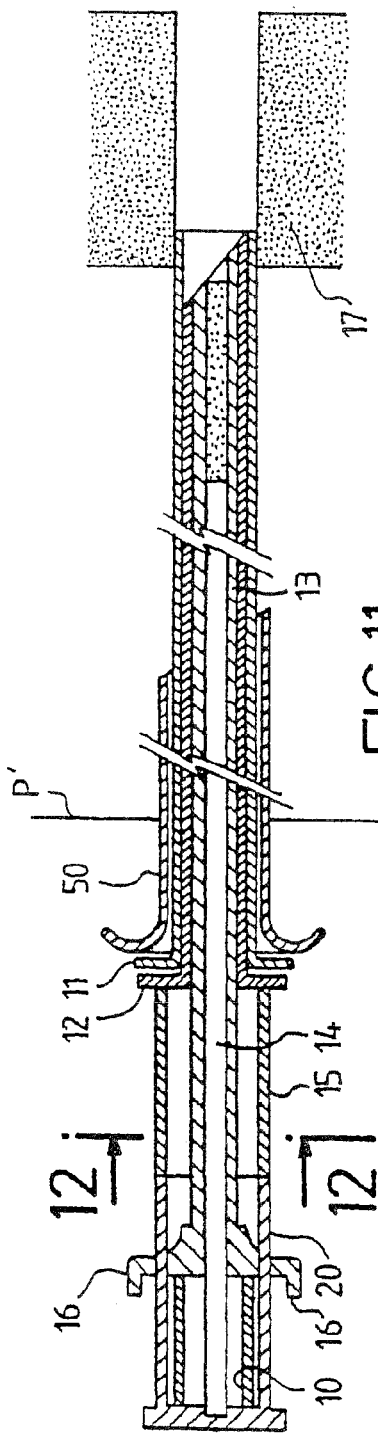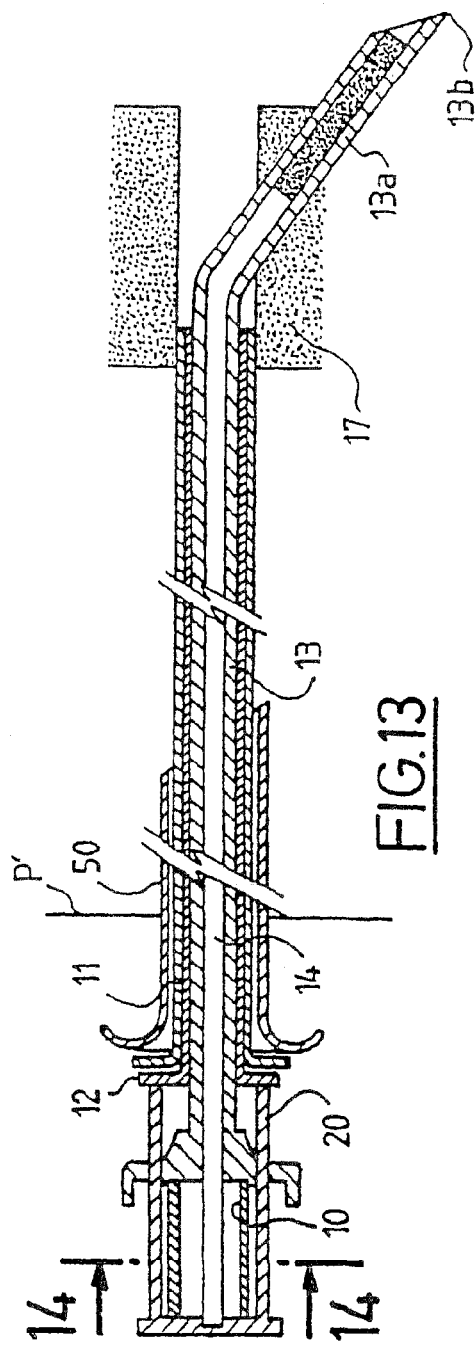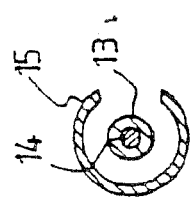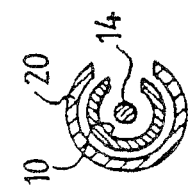

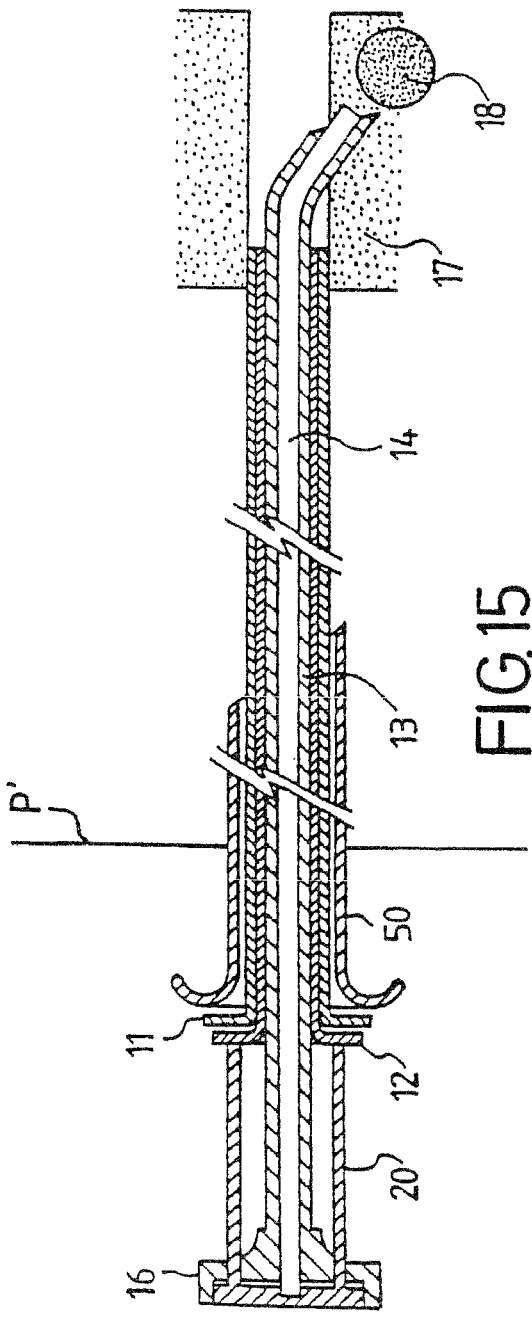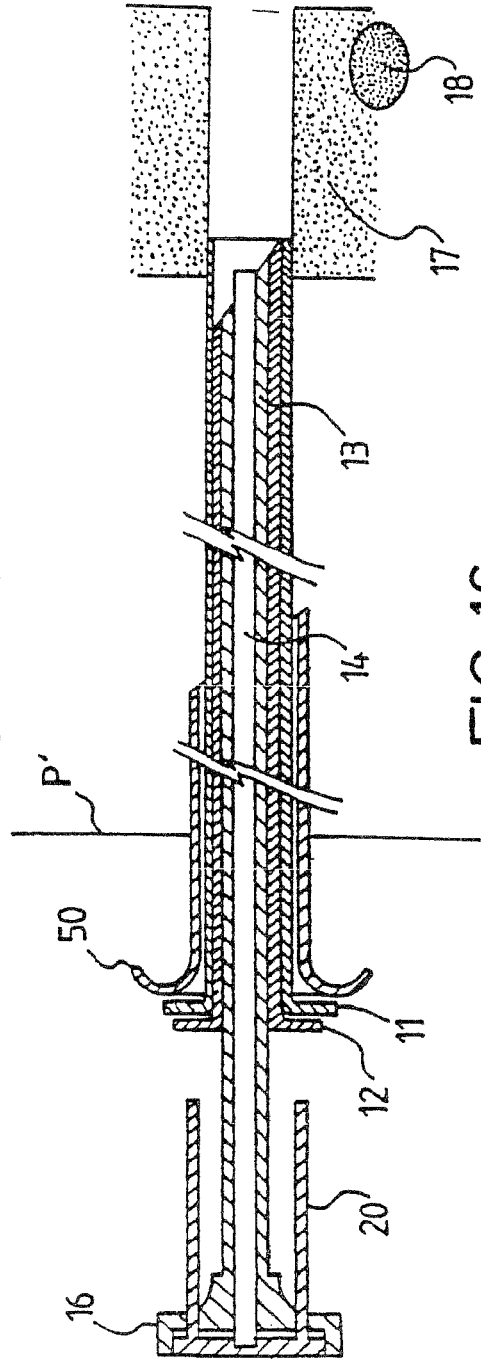

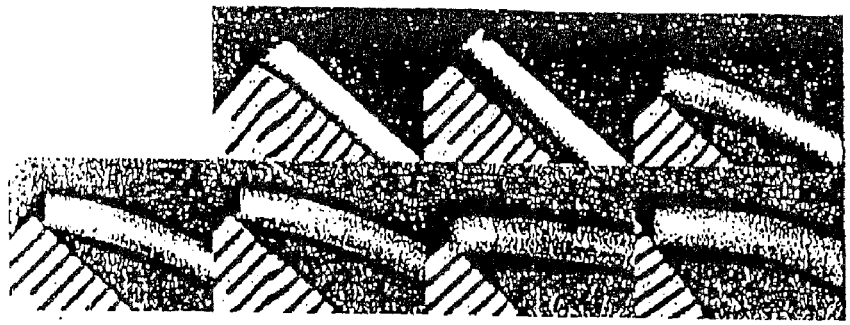
t−0,1h,1j,2j,3j,7j,10j
FIG.30
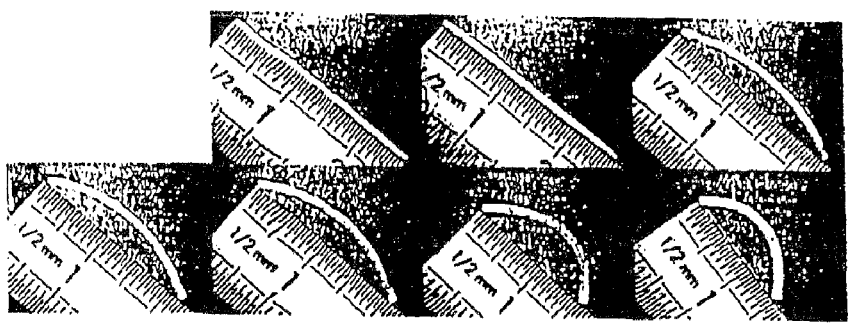
t−0,1h,1j,2j,3j,7j,10j
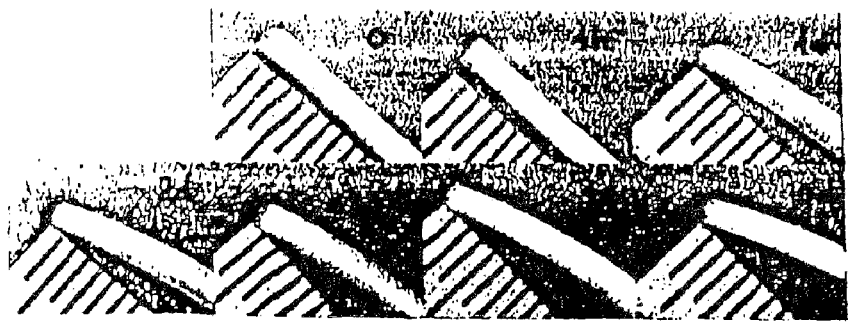
FIG.31

DEVICE FOR LOCAL ADMINISTRATION OF SOLID OR SEMI-SOLID FORMULATIONS AND DELAYED-RELEASE FORMULATIONS FOR PROPOSAL PARENTERAL ADMINISTRATION AND PREPARATION PROCESS

This is a divisional of application Ser. No. 10/060,146, filed Feb. 1, 2002, now abandoned, which was a continuation of application Ser. No. 09/319,159, filed Jul. 21, 1999, now abandoned, which was a 371 National Stage application of International application no. PCT/FR97/02182, filed Dec. 2, 1997, which claims priority to French application no. 96/14755, filed Dec. 2, 1996. The entire contents of the above-referenced applications are hereby incorporated by reference in their entirety.

The present invention relates to a therapeutic process for allowing the targeted treatment of non-liquid pharmaceutical formulations as well as the preparation and the device designed for carrying out the process.

BACKGROUND OF THE INVENTION

The advantages of the use of a local treatment or administration when the active principle (AP) is in this way preferentially directed towards its site of action are known. It is proved, on the other hand, that oral or parenteral administration of a medicament and its systemic diffusion can, in certain cases, not give a satisfactory result. In addition, even in the case where a general or systemic treatment is aimed at, especially in the case of delayed-release formulations, it is of interest to insert the formulation into a suitable site.

Apart from the improvements in the local efficacy, the local treatment with respect to a general treatment above all allows the doses and the secondary effects, especially linked to the AP, to be decreased in the sites of the body where its presence is either useless or harmful.

The local administration of a medicament thus allows the therapeutic index of the product to be improved while decreasing, if need be, its general toxicity and the risk of systemic effects.

The cutaneous, ocular, naso-sinusal, pulmonary or even gastric or rectal topical forms were the first non-parenteral forms to use local administration. When the depot site of the formulation is accessible with relative difficulty or necessitates an invasive form and when the treatment must be repeated, or even more, chronic, even if the advantage of targeting is known, in practice its use comes up against the difficulty or even the discomfort of a repeated therapeutic action.

On the other hand, the advantages of the use of a sustained-release or delayed-release formulation which allows, in a single administration, the sick person to be given his/her medicament for several days, several weeks or several months, is known.

This delayed-release form improves compliance when the observance of the treatment does not depend on the sick person or the care personnel but on the preparation. This sustained-release in fact thus improves the comfort of the patient who is no longer constrained by his/her treatment and who thus continuously receives a regular and non-variable dose as a function of taking the medication.

The development of delayed-release forms has led the specialists to consider their local use, especially in the case mentioned above where the depot site is accessible with relative difficulty. The delayed-release form thus avoids having to repeat the administrations or, even more, surgery. In this way, it is possible to hope for significant local concentrations of medicament over a prolonged period without significant systemic doses, thus with fewer secondary effects. This solution is more particularly useful for products which are rapidly metabolized or have a short half-life when they are administered by the systemic route.

Inside the body, targeted and prolonged treatments such as intra- or peri-articular injections of delayed-released corticoids are thus envisaged. Cancers and especially solid tumours are candidates of choice for these local forms which allow the total injected doses of cytotoxic or antineoplastic compound to be decreased, whilst increasing the concentration in the tumour zone to be treated. This is thus capable of avoiding the serious secondary effects of this type of treatment.

Matrix Pharmaceutical proposes a delayed-release preparation based on collagen which will be able to be injected intra-tumorally (IntraDose CDDP-Cisplatin). This formulation is administered in cancers or cutaneous lesions with the aid of a 3 cc syringe and possibly a biopsy needle for the less accessible zones. In a viscous liquid volume which can reach 2 ml, it is thus limited to the initially relatively easy (peripheral) sites or to post-surgical treatments.

It is also possible to mention the MITSUI Patent (FR 2 497 661; JP 562 737) which describes a small rod or needle polylactide-polyglycolide (PLGA) form for local activity, allowing its direct implantation into a zone or an organ inside the body, and, for example, a tumour zone before or after exeresis.

The Gliadel form (Guildford) for its part describes a formulation based on polyanhydride in host form containing carmustine and which can, for example, be deposited at the time of surgery on a cerebral tumour (glioblastoma).

In the present state of medical technology, these targeted treatments inside the body are more often linked to serious surgical operations. They benefit from the prolonged effect of the formulation but cannot be easily repeated.

Chemo-embolization operations are also carried out which consist in injecting, into vessels, suspensions (microspheres), gels or glues with their solvent, which will be able to obstruct a nutrient vascular tract and liberate an AP in a tumour. The occlusion is obtained by deposition after the injection vehicle has left. This technique uses transluminal percutaneous angioplasty catheters to introduce the fluid into the vessel.

The local use of delayed-release forms is also envisaged in certain body cavities and in more accessible sites of the body.

The ®Ocusert system (Alza) is a flexible and oval ocular insert which forms a delayed-release reservoir device comprising an ethylene/vinyl acetate copolymer membrane and which can contain, for example, pilocarpine.

This device is placed in the conjunctival sac and liberates its product according to a zero-order profile. The delayed-release form allows the dose necessary for the same effect on the intraocular pressure to be decreased significantly. The therapeutic efficacy of pilocarpine in the treatment of glaucoma is thus 8 to 10 times better owing to the use of a delayed-release form compared with local drops.

American U.S. Pat. No. 3,545,439 whose contents are incorporated by reference describes an intra-vaginal delayed-release form formed of a ring made using a silicone elastomer and which liberates a medicament for several weeks.

In this case, the local delayed-release administration on the vaginal mucous membrane also allows, according to the AP, a general effect (contraception) to be obtained.

The medical device described by Bukh Meditee (International Patent Application PCT No. WO 89/03232 whose contents are incorporated by reference) allows the introduction into a body cavity of a matrix delayed-release form made of a substance which is poorly penetrable by water and containing an AP.

The delayed-release form combined with the device thus delivers the AP at the local level and during the period of the insertion of the said device. It describes, for example, a catheter for the urethra opening into the bladder combined with an antibiotic delayed-release form capable of preventing infections of the urinary tracts.

For large-volume liquid forms, certain existing processes of local injection could be used. Starting from intraurethral techniques, C. R. BARD, for example, has developed a formulation (Transurethral delivery Kit) which is a syringe containing a solution of collagen in glutaraldehyde which can be easily injected submucosally in volumes of 2.5 to 7.5 ml which form implants without active principle in the context of plastic surgery against incontinence.

The development of intraluminal vascular systems has led to the production of catheters allowing an AP to be liberated locally at their end. Contrary to the catheter which is simply open for liberating fluid, local administration can be obtained with a double-balloon or porous catheter with multiple perforations. This local solution, however, is limited by the time of insertion of the catheter. The pressure of the solution necessary to penetrate the wall also poses a tolerance problem.

For liquid solutions, a true local injection can be obtained in the wall with the aid of an injection system combined with a balloon (Interventional Technologies) or a catheter with a retractable needle (Bavarian Medical Technologies). The administration of the medicament, however, is not prolonged much with these immediate liquid forms.

A part of the device can sometimes be left locally and thus be associated with a delayed-release form. This is the case of the "stents" used, for example, in angioplasty to avoid restenosis, which can be covered by a layer containing an active principle, sometimes with a delayed-release effect. Two essential problems are then posed, the first is the suitability of the released medicament for the specific process of "coating". The second is the limitation of the total dose by the space and the surface offered by the stent.

With heparin, for example, certain studies mention the significance of local treatment to avoid the systemic secondary effects. According to these studies, heparin inhibits the proliferation of smooth muscle cells after endothelial damage. Its systemic administration, in adjacent subcutaneous or local delayed-release form external to the vessel, always leads to a decrease in the neointimal proliferation but the local form is the only one not to involve systemic perturbations of coagulation.

It would even be possible to cite osmotic pumps which are used to validate prolonged local administrations with, as a major disadvantage, their surgical implantation. For this reason, they are not presently used in man.

All these examples indeed show the interest and the advantages brought by a targeted treatment, above all if it can be prolonged.

These technical solutions, however, all have certain disadvantages amongst which the most important are the lack of versatility of the solution retained, the association with a specific device which remains totally or partially inserted over the period of release of the medicament and, finally, the limits of the injectable volume, thus, of the dose of AP.

Each of these solutions allows only one or several particular cases in a well-defined site of the body to be treated.

Vectorization by local administration is sometimes described as first generation with respect to the "prodrug" and vector (liposomes . . . ) formulations called second generation or to macromolecular recognition systems or "site-specific" activation called third-generation. These solutions, even more than the present local administration techniques, however, are very specific, not always applicable and sometimes not very precise.

The aim of the invention is to propose a process solving the present major disadvantages of local administration or vectorization by flexible endoscopic surgical techniques (fibroscopy) or rigid endoscopic surgical techniques (endoscopy) and of interventional radiology (active or non-active catheter).

The non-dispersed solid and semi-solid formulations have the advantage of offering a minimal volume for a quantity of AP corresponding to a treatment dose. The solid and semi-solid delayed-release forms can thus allow several days of treatment in a volume of a few microlitres.

The local administration of a treatment allows the total therapeutic dose for the same effect to be decreased significantly.

The combination of a solid or semi-solid delayed-release form and of a local administration thus leads to the production of micro-dosages particularly adapted to local deposition at spaced intervals of time.

The present development of imaging, optical and micromechanical techniques applied to medicine in the field of intravascular or cavitary instrumentation and of minimally invasive surgery has led to the design of more and more fine and more and more precise tools allowing very deep local intervention in the body with minimal trauma and thus of multiplying the accessible sites.

SUMMARY OF THE INVENTION

The invention thus proposes a process, a device and a formulation suited to the progress and to the miniaturization of pharmaceutical and medical technologies.

The process aimed at by the invention for the implantation or the insertion of an active principle contained in a solid or semi-solid formulation in a precise administration site of the body is characterized in that it consists in obtaining the solid or semi-solid formulation, in loading this formulation into a device which can be operated outside the body, in bringing the said device to the said depot site inside conventional tools of intervention at this level, and in inserting or implanting the said formulation by operating the said device.

According to other features of the invention:
the said depot site is not accessible with a syringe or a conventional hypodermic trocar,
the said solid or semi-solid formulation has a thin and elongated shape once filled into the said device,
the said device is thin and elongated to be able to move in the said conventional tools of intervention,
the said solid or semi-solid formulation is a delayed-release formulation,
the said thin and elongated shape gives a minimum length to diameter ratio of 10,
the said device is that containing the said formulation exactly fitted to the said shape,
the said shape and the said device are cylindrical,
the said implantation takes place in a tissue, in a mucous membrane or an internal wall of the body by the cavitary route,
the said implantation takes place in a tissue, in a mucous membrane or an internal wall of the body by the vascular, arterial or venous route,
the said implantation takes place in a tissue, in a tumour or a pathogenic zone by the surgical route, the said insertion takes place in a body cavity or in an organ by the cavitary route, the said insertion takes place in a body cavity or in an organ or a tissue by the invasive or surgical route, the said active principle is an anti-inflammatory, the said active principle is a peptide or a peptide analogue, the said active principle is an anticancer product, the said active principle is a mixture of 2 or more active principles.

The invention also relates to:

a method of therapeutic treatment in which an active principle in, a solid or semi-solid formulation is inserted into a body cavity so that the active principle is liberated in the fluids at the surface of the said cavity and should be able to act locally towards the sites of drainage of the said body fluids, a method of therapeutic treatment in which an active principle in a solid or semi-solid formulation is implanted into a mucous membrane or an internal secretory tissue of the body such that the said active principle is liberated and excreted with the natural fluids and should be able to act locally or towards the sites of drainage, a method of treatment in which the said active principle has a local and/or systemic action from the administration site of the implant, a method of therapeutic treatment of ORL pathologies in which the active principle in a solid or semi-solid formulation is introduced into a cavity of the face or into the mucous membrane which covers it, a method of therapeutic treatment in which the said active principle is a corticoid, a method of therapeutic treatment of conditions or vascular, venous or arterial treatments in which the active principle in the solid or semi-solid formulation is introduced into, or around, the vascular wall by intraluminal injection.

The pharmaceutical and medical aspects of the invention join in the search for a fine and miniaturized system which can be easily positioned and operated in any of the zones of the body from transluminal percutaneous angioplasty catheters, endoscopes or any other invasive device which is sufficiently thin and long to reach the zone of administration. The shape (thin and long) of the formulation in the administration device facilitates its local administration. This characteristic of the system under its pharmaceutical and medical aspect will allow its general use.

If insertion is understood as meaning a form deposited in the surface and by implantation or an injection into a tissue, the targeted, even prolonged, treatment will be able to be inserted inside a natural cavity of the body if this is capable of acting as a natural reservoir, that is to say if the form of the administration of medicament allows it to stay in the body cavity at least over the time of its release. It will be possible for this form to be the elongated form studied to facilitate its deposition with the device, or its production once deposited.

The shape of the device and of the formulation is thus not adapted a priori to the zone of insertion as the Ocusert, vaginal ring or the stents can be. The shape of the formulation, however, can develop after administration to facilitate its local maintenance. After its administration, the formulation is not combined with all or part of the deposition device but left on its own at the depot site.

If, for a specific need and therapeutic period, insertion into a natural cavity of the body is not desirable, the targeted, or even prolonged, treatment will also be able to be implanted inside a target tissue of the body to allow its administration over the release period.

It will be possible to carry out this implantation with the device combined with conventional tools, by the transcutaneous route or by the vascular or cavitary route in a mucous membrane or a wall of the body or by the surgical route in a target tissue.

The insertion of the delayed-release form will allow a local, superficial or external treatment, but also targeting for a deep effect, or even for a systemic effect, for example with a deposition to the mucous membranes.

In the same way, the implantation of the delayed-release form will allow general treatment but also targeted treatment by local hyperconcentration or by excretion.

Thus, according to the therapeutic applications and the zone, insertion, like implantation, will be able to be a systemic solution, an internal local solution or, finally, an external targeting solution.

It will be possible for the immediate or delayed-release solid or semi-solid formulations used in the process of the invention to be any solid or semi-solid formulations whatsoever capable of being able to be made or packaged in the form and the volume compatible with the process and the injection device.

Thus, it will be possible for the solid or semi-solid formulations preferentially to be formulations produced from biodegradable excipients such as, for example, inorganic salts (calcium, magnesium, bismuth, zinc); lipids; carbohydrates (polysaccharides, sucrose, glucose, agarose, dextrin, cyclodextrin and mixtures); proteins (gelatin, modified collagen, albumin, casein, derivatives and mixtures); natural and synthetic polymers (polyisobutyric acid, polylactic acid, polyglycolic acid, polylactide-polyglycolide copolymer (PLGA), polyester, polycaprolactam, polyethylene glycol, polypropylene glycol, ®Pluronics, polyanhydrides and their mixtures).

It will be possible to produce the solid or semi-solid formulations without excipient or structured with small quantities of injectable excipient of manitol, hyaluronic acid, cellulose derivatives type etc.

It will be possible to produce the semi-solid formulations by mixing the AP with or without excipient, with water, an organic solvent, oil or any other injectable liquid capable of giving the semi-solid form.

The solid or semi-solid formulations will be either immediate formulations or delayed-release formulations.

It will be possible to produce the solid immediate formulations as indicated in the SCRAS patent (Delivery of Solid Drug Compositions WO 96/07397). It may be possible to produce the delayed-release semi-solid and solid formulations according to the formulation and the process claimed by the SCRAS patent (Sustained Release of Peptides from Solid and Semi-solid pharmaceutical compositions WO 96/07398 whose contents are incorporated by reference).

The solid or semi-solid formulations will advantageously be produced according to processes allowing a high concentration of active principle of greater than 20% or even greater than 40%, preferably of greater than 50% and up to 100% of AP.

Before their deposition, the non-dispersed solid formulations according to the invention will have a thin and elongated shape: rod, implant, pellet, stick or needle, so as to be able to be introduced inside the implantation device which will itself be able, if necessary as a function of the depth of the injection into the body, to be inside an endoscope or a catheter. The dispersed solid formulations (powders, spheres) will have to be able to be arranged longitudinally in the device.

The solid formulations in the device will thus preferentially have a maximum diameter of 3 mm and advantageously a diameter of less than 2.5 mm or even a diameter of less than 2 mm, preferably of less than 1 mm. As a function of the total dose and above all for the immediate forms or the short-duration or low-dose forms (less than 0.1 mg/day), it will be possible for the diameter of the solid forms to be even smaller and down to 0.1 mm.

It will be possible for the smallest diameters, in certain cases, to have a technical advantage to facilitate deep local implantation; however, with catheters and endoscopes, a greater diameter will not have the same disadvantages (especially in terms of comfort of the sick person) as in the case of trocar-type superficial injections (Zoladex, trademark registered by Zeneca) or mini-trocars (Auto-injector, Retro-injector- Needle-less Parenteral Introduction Device WO 96/08289 whose contents are incorporated by reference) or because the use of medical devices necessitates, in addition, local or general anaesthesia, or alternatively because the deep implantation zone is less sensitive than the skin.

It will be possible for the solid forms to have a length of a few centimeters, in general of less than 3 cm and preferentially of less than 2 cm and suited to the space in the depot zone.

The solid forms will preferentially be cylindrical and obtained by extrusion techniques.

The semi-solid forms according to the invention will have a sufficiently high viscosity to contain a high concentration of AP (preferentially greater than 20%) and to remain homogeneous while allowing deep injections through the needle of the device of the invention.

It will be possible for the semi-solid forms to be gels, oils, pastes or any other semi-solid dispersion of an AP in a liquid vehicle.

The semi-solid forms will have a low total volume, in general of less than 300 µl and preferentially of less than 100 µl or even less than 50 µl.

The process and the devices according to the invention will preferentially use injectable excipients which are biodegradable or normally eliminated or solubilized in the body fluids.

However, it will be possible for the process to use devices or formulations based on non-biodegradable biocompatible biomaterials when the site and the deposition tools will easily allow the withdrawal of the said device or of the said formulation after its action, that is to say rather for inserts than for implants. The device or the formulation will have to have a thin and elongated shape, like the other solid forms compatible with deep local administration like, for example, Norplant silicone implants, PHEMA reservoir systems from Hydromed, or even Duros osmotic pumps from Alza.

The devices according to the invention correspond to the solid or semi-solid formulations combined with the localized deep insertion or implantation device.

The device according to the invention for the implantation or the insertion of an active principle in a solid or semi-solid formulation into a precise administration site of the body is characterized in that it comprises a part placed inside the body of the patient with means of packaging of the solid or semi-solid form, means of positioning to the depot site, means of injection or of insertion at this depot site and means of withdrawal after injection or insertion, and a part left outside with means of operation of the functions of the device.

According to other characteristics:
the means of packaging of the solid or semi-solid forms are also the means of positioning and of injection,
the said device comprises a piston inside a guide which can be operated in a trocar or a catheter,
the means of packaging, positioning and injection is a needle,
the said needle once operated can be orientated with respect to the device by elastic preshaping or preconstraint or by mechanical means,
the external means of operation of the device allow, in a sequential fashion, the injection of the needle, the advancement of the piston as far as the bevel of the needle to deposit the solid or semi-solid form, the withdrawal of the needle around the piston and the combined withdrawal of the needle and of the piston,
the sequential operations of the device from external means are controlled remotely and in order with the aid of two movable stops of which the first is arranged on a push button coaxial to the piston, and the second is a tubular piece inserted between the guide and the push button.

It will be possible for the devices to be used directly or combined with the medical instruments for local therapy (endoscope, fibroscope, tube, catheter, spike, aerator, cannula, perforator, trocar . . . ).

The devices will be introduced at the local level and will allow the insertion or the implantation of the semi-solid or solid forms. They will be withdrawn immediately after this deposition.

Like the formulations, the devices used according to the process of the invention for deep local administration of solid or semi-solid formulations will be versatile and of low volume with a suited thin and elongated shape.

The devices will thus preferentially have a maximum diameter of 3 mm and advantageously a diameter of less than 2.5 mm or even of less than 2 mm. As a function of the formulation, it will be possible for the diameter of the device to be even smaller and down to 0.3 mm.

In a fibroscope or an endoscope comprising, for example, 4 channels (video, instruments, introduction and withdrawal of fluid, illuminated optical fibres), it will be possible for the insertion or implantation device, like a conventional tool (biopsy forceps style) to occupy the channel of the instruments, which frees the channel for introduction of fluids or even allows its elimination. In this case, it will be possible for the devices to have a diameter of less than 2 mm and, for example, of 1.7 mm like certain instruments.

In a catheter, it will be possible for the insertion or implantation device, like the device for insertion of stents, to occupy the channel and to be operated from the exterior in situ. In this case, it will be possible for the device to have a diameter of less than 2.5 mm and, for example, of 2 mm like certain stents.

In a trocar, it will be possible for the insertion or implantation device, like the perforation device, to occupy the lumen of the trocar. It will be possible for the device to have a diameter of less than 3 mm and, for example, of 2.5 mm like certain perforators.

Other characteristics and advantages of the invention will become clear from the description which will follow, made with reference to the annexed drawings which illustrate several embodiments by way of non-limiting examples.

BRIEF DESCRIPTION OF THE DRAWINGS

FIG. 1 is a view in longitudinal elevation of a first embodiment of the administration device of solid formulations according to the invention in the case of the administration of the formulation inside a natural cavity of the body, used as a reservoir for, release of the formulation.

FIGS. 2, 3 and 4 illustrate a sequence of employing the device of FIG. 1 to administer a solid formulation locally in the body.

FIG. 5 is a half-longitudinal section half elevation view of a second embodiment of the device for administration of formulations according to the invention, shown partially introduced into the body of a patient ready for the administration of the solid formulation.

FIG. 6 is a transverse sectional view along 6/6 of FIG. 5.

FIG. 7 is a view analogous to FIG. 5 showing the device after pushing of the solid form outside a guide of the device, ready to be deposited in the body of a patient.

FIG. 8 is a transverse sectional view along 8/8 of FIG. 7.

FIG. 9 is a view in elevation analogous to FIGS. 5 and 7, showing the device after partial withdrawal of the needle, the solid form remaining in place in the body.

FIG. 10 is a view analogous to FIG. 9 showing the needle and the piston inside this completely returned.

FIGS. 11 to 16 are views similar to FIGS. 5 to 10 respectively but in which the device is used to administer a semi-solid form.

FIG. 30 shows photographs of Triptoreline acetate PLGA (75:25) formulations with 20% of active principle placed in a physiological medium in vitro after one hour, 1 d, 2 d, 3 d, 7 d and 10 d.

FIG. 31 shows photographs of Triptoreline acetate PLGA (75:25) formulations with 52% of active principle placed in a physiological medium in vitro after one hour, 1 d, 2 d, 3 d, 7 d and 10 d.

DETAILED DESCRIPTION OF THE INVENTION

Figure 17:
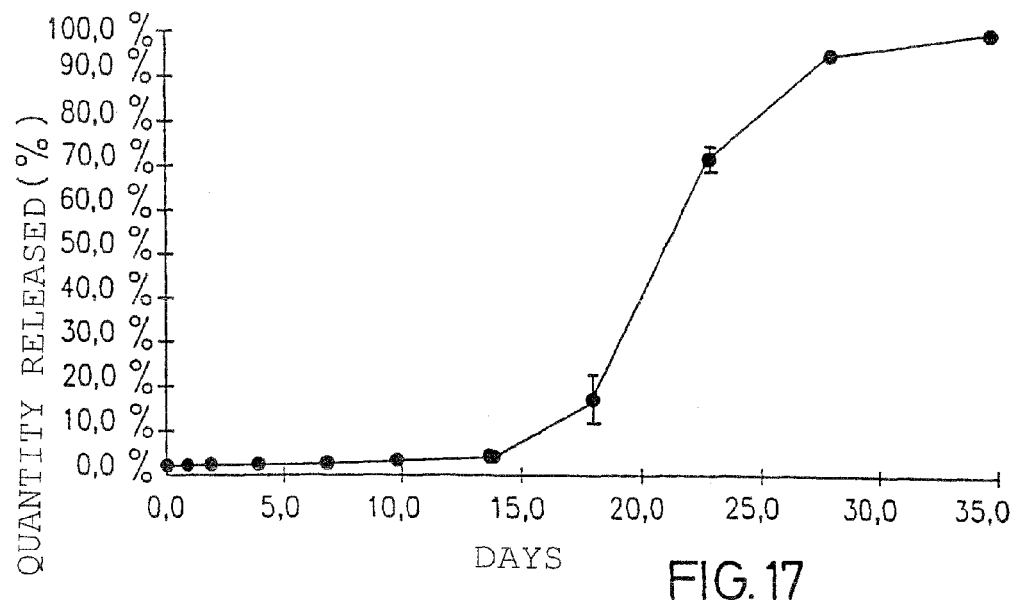
FIGS. 17, 18 and 19 show the release in vitro of inserts of dexamethasone at a respective concentration of 10, 15 and 20%.

The administration device of a solid form 1 represented in FIG. 1 comprises a tubular guide 2 containing a piston 3 which is able to push outside the guide 2 the solid form 1 contained at the end of the latter. The guide 2 and the piston 3 are provided, at their opposite ends, with respective manual handling collars 4, 5.

FIG. 2 illustrates a possible example of the invasive system in the body of a patient for the employment of the device for administration of the solid form 1 of FIG. 1. The invasive system is, in the example of FIG. 2, a trocar 6 containing a perforator mandrel 7, if the access to the natural cavity of the body used as a reservoir for release of the solid formulation 1 necessitates a perforation of internal tissues. In FIG. 2, the invasive system is shown partially introduced inside the body in its part situated to the right of the plane L, while its part situated to the left remains external.

If the access to the natural cavity of the body does not necessitate a perforation of internal tissues, the invasive system can be an endoscope, a fibroscope or a catheter (not shown). The invasive system used is introduced into the body cavity (sinus of the face, oesophagus, trachea, vessel, etc.), with the aid of the perforator mandrel 7 in the case of a system such as that of FIG. 2. The mandrel 7 is then withdrawn from the trocar 6 (or from the endoscope, from the catheter, etc.) and the administration device of FIG. 1 is introduced inside the trocar 6 (FIG. 3), until the collar 4 of the guide 2 comes up against the bent annular end 8 of the trocar 6.

It is then sufficient to push the piston 3 to eject the solid form 1 outside the guide 2, because no tissue resistance opposes its movement (FIG. 4).

In the second embodiment of the device for administration of a solid form 9, illustrated in FIGS. 5 to 10, this device is intended for the case of an injection of the said device inside a tissue, a wall or a mucous membrane from an internal invasive system already inserted into a cavity as shown in the drawings, but also from an invasive system inserted in an internal tissue.

The invasive system comprises a tubular piece 50 partially inserted in the tissue through the surface P' of the latter, and a tubular guide 11 which can be a fibroscope or an endoscope, in which a catheter 12 can be mounted. The latter forms a guide for the administration device formed by a needle 13 and a piston 14 for extraction of the solid form 9 in the tissue 17.

The device has two movable stops (10, 15) of which the first 10 is a sleeve arranged in a push button 20 coaxial to the piston 14, this stop 10 and the push button being longitudinally truncated (FIG. 8); the second is a tubular piece 15, likewise truncated (FIG. 6), interposed between the catheter 12 and the push button 20.

The injection of the administration device 13, 14, 9, can be obtained by moving the guide backwards, but is preferably carried out as illustrated in FIGS. 7 to 10, in the following manner. The stop 15 is withdrawn; the needle 13 is moved with the aid of the push button 20 containing the stop 10 (FIG. 7). If necessary and as illustrated in FIG. 7, especially in the case of vessels, the needle 13 can have at its end a bent shape 13a obtained by liberation of an elastic preconstraint of the needle 13 in the guide. Once the constraint of the guide is liberated, the bent end 13a facilitates the oblique injection of the solid form 9 into the wall or the mucous membrane 17. It will be possible to obtain or set this angle between the needle and the guide by any other mechanism customarily used by these devices.

Once the solid form 9 and the bent end 13 a have been injected, the stop 10 of the push button 20 is removed, and the needle 13 is withdrawn by traction on the lugs 16 without moving the piston 14 in order to deposit the solid form 9 in the tissue 17 (FIG. 9). When the bevel 13b of the needle 13 reaches the end of the piston 14, the latter is withdrawn with the needle 13, leaving the solid form 9 in place, this movement being obtained by traction on the push button 20 and the lugs 16 (FIG. 10).

The device of FIGS. 5 to 10 can likewise allow the administration of a semi-solid.

The administration device illustrated in FIGS. 11 to 16 is similar to that of FIGS. 5 to 10 and only differs from it by the fact that the piston 14 acts on a non-solid form 18, in appertaining to a microsyringe up to the point of the injection device.

Here also, the invasive system 9, 11, 12 can be inserted in an internal tissue 17.

The administration process here consists in injecting by pushing it outside the guide 9, 11, 12 the administration device formed of the needle 13, the piston 14 and the semi-solid form 18. The needle 13 can possibly be bent as in the embodiment of FIGS. 5 to 10. The piston 14 is moved in the needle 13 to inject the semi-solid 18 (FIG. 14) in the same manner as in the preceding embodiment.

The piston 14 and the needle 13 are finally withdrawn together by reintroduction into the guide 11, 12 by traction on the lugs 16 and on the push button 20 (FIGS. 15 and 16), the semi-solid form 18 left in place in the tissue 17 then being able to assume a spherical or ellipsoidal form.

The drawings of FIGS. 1 to 16 are to allow the administration processes for different specific treatments described further on to be illustrated. These different specific treatments according to the process of the invention of solid or semi-solid local administration involve the employment of the process in order that it can be carried out and thus offer certain novel therapeutic solutions which are part of the invention. These different examples illustrate the possible field of application of the invention, but do not form an exhaustive list of applications of the process and are thus not limiting.

Of the number of possible treatments, according to the process of the invention, it is possible to mention anaesthetic, analgesic, anti-inflammatory, cancerological, cardiological, endocrinological, rheumatological etc. . . . treatments as well as the combined treatments. Of the number of endoscopic or radiological techniques capable of allowing this local treatment process, it is possible to mention urology, gynaecology, arthroscopy, ORL, bronchoscopy, gastrology, minimal invasion or even cardiovascular surgery.

These processes are novel because they use a low volume (microlitres) solid or semi-solid, delayed-release or non-delayed-release pharmaceutical formulation. This formulation differs from existing local treatments which use large-volume specific solid forms or liquid or suspension forms.

According to this process and with these non-liquid formulations, the formulation is not studied in its composition or in its form for precise vectorization. On the contrary, the formulation is studied for a tool or device suited to internal local administration and which allows remote injection or in-situ insertion.

It would be possible for the process to use, in this pharmaceutical form and with these tools, conventional APs and especially those having already demonstrated their local administration interest, or whose local interest can be deduced from the mode of action of the AP, even if its use in this form does not yet exist, especially when it could not easily be employed without the contribution of the invention. The different examples which follow illustrate the possibilities of this process.

The process, the formulations and devices allow administration into body cavities and intratissue administration. Whatever the cavity or tissue, the advantage is to be able to lead the formulation to the depot site while avoiding or while decreasing the tissue lesions.

It will be possible for these natural cavities to be used as therapeutic product reservoirs, especially if their anatomy allows the "imprisonment" of the formulation. The process allows, for example, administration into natural cavities of the face and into its tissues. With certain APs, the whole of the objectives stated above are found with this treatment (better local efficacy, decrease in dose, increase in the duration of action, improvement in comfort and compliance, decrease in the secondary effects).

It will be possible for the intra or perisinusal inserts or implants to transport the AP into the mucus owing to the ciliary flows of the mucous membranes or to allow its local systemic diffusion by contact. It will likewise be possible to envisage a general action by progressive diffusion towards the digestive tracts for medicaments necessitating taking low doses daily.

The local corticoids are a good example of a local action product having disadvantages by the general route. However, the existing local treatments (drops, spray etc.) run up against anatomical arrangements to reach a precise target zone such as the meatus medius (monocellular sulcus). In addition, with these existing treatments, the necessary persistence of the AP locally involves frequent applications.

This therapeutic process according to the invention allows this key zone of naso-sinusoid pathology to be reached. In addition to the maxillary sinuses, according to needs, it will be possible to treat locally the ethmoidal cells, the sphenoidal and frontal sinuses, and the cavum tympani. The implanted or inserted solid or semi-solid delayed-release form will be in contact with this mucous membrane which secretes and is covered by mucus circulating on the meatus towards the nasal fossae, and emptied towards the cavum by passing in contact with the tubal splenium and the Eustachian tube.

The process will allow, for example, the concentration of therapeutic product in the monocellular sulcus which is the seat of pathologies, in particular inflammatory, to be increased and maintained. If the delayed-release non-liquid form is deposited in the interior of the sinuses, it will be possible to use a device according to the drawing of FIG. 1 which will be able to be positioned with the aid of conventional otorhinolaryngology drainage tools (ORL; trocars, tubes). It will likewise be possible to inject the formulation into the mucous membrane of the nasal fossae, into the turbinate bones or into the tubal splenium with the aid of the device shown in FIGS. 5 to 16. According to the zone of deposition, is and the formulation, the action will thus preferentially be external, intratissue or systemic.

In ORL, it will thus be possible to treat, for example, by corticoid therapy, naso-sinusoid polyposis, allergic or non-allergic rhinitis, certain types of otitis or non-infectious sinusitis etc. In addition to anti-inflammatory treatments, it will be possible to practice antibiotic, anti-allergic, immunostimulant, etc. treatments. It will likewise be possible to combine the treatments. These treatments will have a local aim.

It is possible, for example, to make rods of dexamethasone phosphate matrixed to a level of 15% in PLGA 50-50 according to the following steps: weighing of the raw materials, mixing of the two powders, extrusion, dosage, packaging and sterilization. It will be possible for the implant obtained to have an average diameter of 2.4 mm for a length of 12.5 mm. It will be able to be introduced inside the maxillary sinuses with the aid of the device shown diagrammatically by FIG. 1. It will Likewise be able to be implanted in the mucous membrane of the turbinate bone with the aid of the device shown diagrammatically in FIGS. 5 to 10.

This solid formulation is a 1-month delayed-release formulation which contains 7.5 mg of dexamethasone and which releases on average 0.5 mg/day with an implant in each sinus. For chronic treatment, it would be possible to imagine the intrasinusoid use of a polymeric form (PLGA 75-25) of three months' duration of action, or even a reservoir form (Hydromed type) of 1 year's duration of action.

It will be possible for these delayed-release preparations to be used in the ambulatory case on patients suffering, for example, from chronic nasal obstruction. The medical action for the intrasinusal administration will appertain to the current ORL actions which can be practised in the doctor's surgery: trocar puncture with or without anaesthesia. It will or will not be possible to prepare the route first (meatotomy, spikes, drains or others).

Deep injection localized in the turbinate bone or the mucous membranes of the nasal fossae will also be easy with the aid of the device which is or is not combined with the customary tools of endoscopic exploration. In the nasal fossae, local administration is not very deep. According to the body cavities or the site of endoscopic surgery, it will be possible for the distance between the external zone and the internal depot to be even shorter or much larger.

Delayed-release corticoids are already used in rheumatology. It is possible, for example according to the process, to imagine an intra- or periarticular local injection with delayed-release form deposition in low volume (corticoids, anti-inflammatories) at the site of inflammation (tendinitis, bursitis, non-infectious arthritis, arthrosis, etc.).

It is also possible, according to the process, to imagine an ocular treatment by depot injection into the mucous membrane under the eyelid. The small volume of solid or semi-solid forms will make this depot insensitive and the injection will at the same time favour the delayed-release effect and the local maintenance of the treatment in a more efficacious manner than the depot in the conjunctival cul-de-sac which is amply drained. Above all, this approach is advantageous for a chronic treatment such as, for example, glaucoma, with pilocarpine.

Here, the injection is virtually superficial and does not necessitate tools apart from the administration device for the microvolume semi-solids or solids.

In the same way, it is possible according to the process of the invention to treat certain superficial tumours or cutaneous problems by local, intradermal or hypodermic deposition.

For example, it will be possible to use dermopeptin (BIM 23014C) in a 20% semi-solid delayed-release form in water and under a volume of 20 micro-litres or a total dose of 4 mg of Somatuline. It will be possible to inject the formation at the cheloid or melanoma level, thus creating a high and sustained local concentration from a diffusion gradient zone at the site of injection.

In the case of certain solid tumours, it will be possible to combine the treatment with a cytotoxic agent (5FU or cisplatin type) whose diffusion will be regulated by the same local form and whose local concentration will thus be very high with a very low total dose.

It will likewise be possible to use the same formulations in much deeper applications and, in that case, combined with SMA (Shape Memory Alloy) active catheter type or fibroscope tools, and with specialities such as interventional radiology or endoscopic or robotic surgery.

It will be possible, for example, to implant intracerebrally a BIM23014C delayed-release form which is more cytotoxic owing to access into the cranium.

The solid or semi-solid forms according to the invention have the advantage, with respect to the Gliadel-type local treatment, of being able to be administered without trepanation at the superficial level, but likewise deeply with the aid of stereotactic, endoscopic and robotic neurosurgery.

The solid tumours treated, for example, with the collagen forms of Matrix will be able to be treated in the same way with these microdosages. Whatever the solid or semi-solid form, the advantage of the volume allows vectorization into all the sites and avoids the risk of spreading caused by the injection of a liquid volume of a few millilitres.

It is always possible with a solid or semi-solid form localized more deeply in the body, after transluminal percutaneous angioplasty, to treat local intravascular restenosis. With respect to local treatment combined with the stent, the advantage of a treatment according to the process is to not be confronted with the dose limit of the vascular space and of the surface of the device, and of not entering into direct contact with the damaged vascular wall, while allowing a high local concentration in all the layers of the vessel and around, and a systemic effect if necessary.

It will be possible, for example, to inject angiopeptin alone or combined with heparin according to the diagram of FIGS. 5 to 16. It will be possible, of course, to inject any other single or combined AP capable of avoiding the risks of restenosis and of favouring the result.

With respect to this perivascular therapy, it is likewise possible to mention the possible use of semi-solid intravascular forms with the same objective as chemo-embolization by suspension, glue or gel. The advantage here is to use a delayed-release form whose volume (thus the depot zone) is pre-established; this allows a better localization of the occlusion in the vessel.

The process and the devices according to the invention combined with the fibroscope or with any other direct or indirect imaging solution allow administration in the organic walls.

For example, when an intervention is made at the level of the bladder by the urethral route, it is possible to imagine the implantation of a treatment (prophylaxis, antibiotic, etc.) in the thickness of the urethra.

It is possible to reach the trachea and the bronchi (stents). According to the process, it is thus possible to envisage a pulmonary treatment either by administration of a solid or semi-solid form to the lung or by implantation in the mucous membrane of the bronchi or of the trachea, according to the needs of local intrapulmonary tolerance, it will be possible for the solid form to be dispersed (powder or sphere).

For example, to replace the preventive treatment by inhaled glucocorticosteroids in slight or moderate asthma of recent diagnosis, it will be possible to administer to the lung, via the bronchi, or in the wall which covers them or to cells of the trachea, a delayed-release form of 0.4 mg of budesonide daily which will be secreted in the flow if the form is implanted, and which will be transported by the moisture to the bottom of the pulmonary alveoli. This low-dose preventive treatment, without secondary effect, does not thus pose any observance problem, especially in children. It will be possible for such a form to have a duration of 1 to 3 months, or even more if necessary.

In the digestive tract, devices allowing the local administration of treatment according to the invention are likewise available.

In the oesophagus and in the stomach, it will be possible for the treatment of varices to be envisaged with a form which is local and injected into the wall. In the same way, the tumours at this level which are well individualized and are presently treated, for example, by PCT (photochemotherapy), necessitate, after injection of the photosensitive product, illumination by controlled introduction of a light diffuser at the local level. It is thus likewise possible to inject the anticancer agents directly at this level in solid or semi-solid form with the devices of the invention. It is possible, then, to target even more the zone to be treated and to avoid uselessly damaging the peripheral tissues.

The process of local administration of solid or semi-solid forms involves the sustained presence of a local depot of AP. It is possible, if necessary, to envisage adding to the formulation products favouring local tolerance at the administration site. It is possible, for example, to add very low percentages of dexamethasone, indomethacin, heparin or any other AP capable of avoiding an undesirable local effect.

The mucous membranes or the walls are more permeable than the skin and patch or bioadhesive systems exist which are applied to the mucous membranes (especially buccal or nasal) and which allow a systemic passage of the AP. The disadvantage is sometimes the non-persistence of the formulation in contact with the mucous membrane. It will thus be possible for the sustained presence of the administration according to the process at the local level of mucous membranes or of internal walls to have an advantage in the search for a topical form with systemic activity. It is thus possible, according to the local treatment, to add to the formulation in a small quantity any excipient capable of being a vector of tissue penetration suited to the APs (organic solvents, surfactants, etc.). Thus, it will be possible for a deep local form advantageously to be the site of a systemic diffusion with respect to the buccal or nasal mucous membrane, for example, which would not allow a sustained topical administration.

The process according to the invention will likewise find its application during endoscopic (laparoscopic, arthroscopic, etc.) minimal invasion surgical interventions. The APs used (local anaesthetics, anticoagulants, etc.) can be administered in a solid or semi-solid form with here, again, the advantage of an appropriate microvolume with the reduced intervention space, and the possibility of administration by the instrumental access route.

It will of course be possible to implant with the aid of the process any other solid or semi-solid delayed-release form and especially PLGA implants. It is possible to use them with other peptides, recombinant proteins (interferon), polyclonal or monoclonal antibodies, antisense oligonucleotides or polynucleotides, etc.

The solid formulations or implants which can be used for local administration of the active principle as described above are likewise suitable, through their long and thin shape and their small diameter, for other types of conventional administration, for example for systemic treatment by cutaneous or intramuscular injection.

It has also been very unexpectedly noted that the said solid formulations or implants, especially with a PLGA excipient, having a very significant concentration of active principle, such as described above, whether they are soluble or insoluble, and especially those having a concentration of active principle of between 40 and 100%, and preferably greater than 50%, allow extremely long release times of one month to three months and more, and very regular, or even constant, release rates to be obtained in vivo, in being produced in thin elongated form, of diameter or transverse size of less than or equal to 3 mm, for example 2.5 or 2 mm, or even 1 mm or less, although they dissolve very rapidly in vitro, including when they are used for a local or non-local action.

Conventionally, such rates of active principle were intended for formulations with instantaneous or rapid liberation.

The inventors have additionally discovered that, in a certain form, in homogeneous distribution of excipient, especially of PLGA, it was possible to obtain a delayed-release formulation according to a non-matrix method in which the role played by the excipient was different; this leads to more advantageous formulations whose characteristics are different, which distinguishes them clearly from existing matrix forms.

These non-matrix forms can be described as matrix forms of active principle in which the excipient is dispersed.

The matrix forms employing the PLGA used to date can be either dispersed forms (microparticles) or non-dispersed forms (implants).

Generally speaking, among the delayed-release formulations which have been developed, forms called reservoir forms and matrix forms are found.

The "reservoir" forms use a diffusion barrier or membrane between the active principle and the medium which will serve to control the release of this active principle. The medicament can be inside the reservoir in a solid, semi-solid or liquid form. It can be in solution or dispersed in an excipient. By its porosity, the membrane ensures the controlled passage of the active principle towards the exterior. Among the "reservoir" systems for soluble active principles, it is possible to mention the hydrophilic crosslinked hydroxyethyl polymethacrylate membranes (PHEMA, Hydro Med Sciences). The "reservoir" forms allow a relatively constant level of release of 0 order to be obtained. The principal disadvantage of these reservoir techniques is the necessity of withdrawing the biocompatible but non-biodegradable implant after liberation of the active principle.

The matrix forms use a polymer matrix or system in which the active principle is trapped to be liberated by diffusion, by erosion or by combination of the two phenomena.

The non-biodegradable matrix forms, such as, for example the hydrophobic polymer implants of PDMS silicone type (Norplant, progestational hormones) function only by diffusion. This method of functioning can cause a decreasing release of 1st order when the distance of diffusion increases. The disadvantage is here again the necessity of withdrawing the silicone implant once the active principle has been liberated.

On the other hand, the biodegradable matrix forms do not have this disadvantage since the polymer matrix is eliminated by the body. In addition, this elimination or erosion can participate in the control of the release of the active principle to obtain a constant release.

The most common biodegradable matrix forms currently use polymers of lactic acid or of glycolic acid, copolymers of lactic acid and of glycolic acid (PLGA) or their mixtures.

Thus, EP 52510 whose contents are incorporated by reference describes a PLGA formulation with encapsulation of LHRH or the like which can be a dispersed form of microcapsules produced by coacervation of which the feature is the distribution of the active principle at the centre of the microcapsule with a peripheral PLGA layer.

From EP 58481, whose contents are incorporated by reference, dispersed or non-dispersed formulations of peptides and of PLGA are known, such as implants, in which the active principle is uniformly distributed up to the surface and using a specific PLGA in such a way that the two phases of release (diffusion and degradation) overlap without there being interruption in the release of the active principle.

Numerous other documents relate to the use of PLGA in delayed-release formulations for peptides but also proteins and genes. The patent WO 96/40072 whose contents are incorporated by reference thus describes a preparation of human growth hormone whose stability in the matrix and in the organic solvents used for the microencapsulation is favoured and whose release is ensured by the PLGA matrix. The control process is based on the degradation of the polymer and the opening of pores in the structure which causes it.

All the studies carried out to date agree in saying that the delayed-release control process with the PLGA can cause up to three liberation phases. An initial phase which liberates the active principle by diffusion, a latent phase where no release takes place, and a phase of release of the bound forms correlated with the loss of mass of the polymer.

In all the formulations using PLGA, the control of the delayed-release effect is obtained by matrix mixing of the PLGA and of the active principle so as to allow the polymer matrix to play its role of barrier to the release of the active principle, or even a role in the physicochemical interactions between the active principle and the polymer matrix.

In all cases, this method of release requires a dispersion of the active principle in the biodegradable polymer matrix so as to isolate the loading zones of active principle to the exterior medium and to retain them within the matrix until the biodegradation of this liberates the active principle which is then able to diffuse towards the exterior.

This types of delayed-release matrix form can be easily characterized by making water penetrate it which will hydrate the dispersed zones of active principle and cause a swelling of the formulation under the effects of hydration by the osmotic forces due to the impossibility of the active principle escaping from the matrix structure.

These phases intermix to a greater or lesser extent according to the PLGA formulation, the degradation of the polymer allowing, for example, the increase in the size of the cavities by which the active principle can diffuse.

Apart from PLGA and polylactic acids mentioned above, very few injectable delayed-release excipients exist. However, it is possible to mention, for example, certain polymers, gels and fatty substances. The polyanhydrides are, for example, polymers whose surface erosion process gives a release profile distinct from that of PLGA and more dependent on the form of the depot than the PLGA which undergoes a global degradation.

Certain delayed-release formulations are likewise found which use collagen or gelatin to obtain a release over time. Other formulations use gels or hydrogels. Matrix Pharmaceutical, for example, uses a viscous injectable gel (AccuSite®, Intradose®).

These formulations formed of a matrix which is less susceptible to isolate the active principle from the medium or more rapidly eliminated in general contain a small percentage of active principle.

Other injectable excipients such as mannitol, polyethylene glycols and hyaluronic acid are likewise used, more often as additives to adjust the delayed- release profile.

Apart from matrix or reservoir techniques, few other approaches today allow a sufficiently long, regular and precise release to be obtained.

It is possible to mention, however, the case of implants which are totally or partially covered by a coating serving as a barrier to the diffusion of the active principle.

In the dispersed or non-dispersed matrix formulations, a certain quantity of active principle is found on the surface of the formulation and is not included in the polymer matrix.

In the dispersed matrix forms, for a given quantity of active principle, the surface active principle represents a high relative quantity with respect to the total of the active principle because of the significance of the surface with respect to the total volume.

To increase the charge or "core-loading" (C.L.) of active principle, there is thus a constraint to inject a large volume of polymer matrix for a given volume of active principle.

This constraint is even more penalizing for the non-dispersed forms or implants because the volume of these for a high quantity of charge necessitates the use of a trocar for the injection of the formulation.

There has indeed obviously been a search to design formulations having a higher C.L., but the experiment has demonstrated the existence of a phenomenon known under the name of percolation which is manifested by a rapid release of almost the whole of the active principle due to the fact that in the polymer matrix the charge zones are found to be in contact with one another, the polymer (PLGA) no longer ensuring its matrix function.

Visually, this phenomenon is manifested after hydration of the formulation by liberation of active principle in a very short delay without swelling of the formulation, the active principle being entrained outside the formulation by the water which circulates in the polymer matrix.

In the delayed-release matrix forms, the type of PLGA and its physicochemical characteristics are clearly specified and determine an area of feasibility. The direct influence of the PLGA on the release by its role of matrix barrier, its role in the relations (hydrophobic, hydrophilic, etc.) with the active principle and the influence of its degradation involve a precise choice of PLGA.

This relation between the PLGA and the release appears clearly, for example, in the duration of action of a matrix formulation.

In such a formulation, the duration of release depends directly on the time of degradation of the PLGA (second phase or rebound) Thus, the PLGAs will be selected as a function of the duration sought. For example, the 50:50 PLGAs, depolymerized in one month, will be used to produce a one-month formulation although necessarily formulations over three months will involve PLGAs whose hydrolysis is slower, for example 75:25 PLGAs.

In the non-matrix formulations of the invention, the excipient, especially the PLGA, does not influence the release and it is, for example, possible to obtain releases over three months with a single 50:50 PLGA which disappears totally from the body in 60 days or even one-month forms with a 75:25 PLGA which will not even have commenced its hydrolysis although all the active principle will be liberated. This is made possible by the fact that the proportion of PLGA is always lower in weight than the proportion of active principle; this signifies that the continuous matrix is no longer the PLGA but the active principle which will thus undergo for the whole of the charge the exterior and especially aqueous influence. It is thus the active principle, especially by the total quantity, which will determine the duration of action.

The invention thus also especially relates to such formulations, whether they are with a systemic aim or for a local treatment, with a conventional dosage or dosage decreased for a local action.

The invention more particularly relates to a delayed-release formulation for parenteral administration comprising a homogeneous mixture of an active principle in the non-dispersed state forming a continuous phase of which at least one part is in direct contact with the exchange surface of the formulation and the exterior biological medium, and of a biodegradable biocompatible excipient, in which the quantity of active principle is at least 50% by weight with respect to the total weight of the formulation, and having a release profile which is independent of the composition of the excipient, of the molecular weight of the excipient or of the active principle/excipient weight ratio, the release profile essentially being exclusively dependent on the total quantity of active principle present in the formulation.

Conversely to known matrix forms permitting a "charge of active principle" in an upper limit of 30% of active principle in order to avoid the phenomena of percolation, the formulations of the invention contain more than 50% of active principle, which represents a decrease in volume of the depot of the order of 3 to 10 times with respect to the volume of the matrix forms.

Thus, in solid form, the formulations of the invention advantageously contain, before as well as after administration, at least 50%, preferably at least 51%, advantageously at least 60% and more advantageously at least 70% and up to 99.999% by weight with respect to the total weight of the formulation, the excipient representing less than 50%, preferably less than 49% and more advantageously less than 30% by weight with respect to the total weight of the formulation.

The excipients are those traditionally used in the solid forms with delayed-release liberations especially the biodegradable polymers.

It is possible to mention, by way of example, the polymers of polylactic or polyglycolic acid type, or the copolymers of polylactic/polyglycolic acid type, or mixtures of these polymers and/or copolymers.

The choice of biodegradable biocompatible polymer forming the excipient is immaterial, this not having an influence on the diffusion capacity of the active principle in the polymer.

It will be possible, for example, to use an injectable fatty substance as excipient of formulations of the invention, such as a polymerized or saturated fatty acid such as ®Compritol or even excipients such as polyvinylpyrrolidone (PVP) or polyethylene glycol (PEG).

The viscosity of the polymers can vary considerably. It has been shown that polymers of low viscosity can be suitable for a method of release of active principle called monophasic. The abovementioned patents EP 58481 and 52510 but also the patents EP 21234 and EP 26599. whose contents are incorporated by reference, put emphasis on low viscosity polymers. These polymers can be suitable for the present invention (for example, viscosity lower than 0.5 dl/g in chloroform). The Applicant has additionally shown in an already filed patent application FR 97 04 837 and in the examples below that unexpectedly, high viscosity polymers, especially higher than 0.5 or even 0.6 and being able to range up to 1.2 dl/g can be preferentially suitable for obtaining a monophase liberation.

It is possible to use DL-PLGAs or L-PLGAs, more preferentially a DL-PLGA produced from 70 to 80% of DL-lactide and from 20 to 30% of glycolide. A PLGA synthesized from 75% of DL-lactide with 25% of glycolide is particularly suitable but other copolymers including 50-50 PLGAs can also be used. It is also possible to use D- or DL-lactide polymers.

The PLGAs can be hydrophilic or hydrophobic. It is possible to produce the formulations of the invention with hydrophilic polymers.

As the biodegradable biocompatible polymer, however, PLGA is preferred, especially a hydrophilic PLGA advantageously having a viscosity in chloroform at 1 g/100 ml of greater than 0.6 dl/g.

The duration of action of the delayed-release formulation will be determined exclusively by the total quantity of active principle which it contains.

Active principle in the non-dispersed state is understood as meaning that the different particles of active principle present in the formulation are mainly physically in contact with one another and up to the surface of the formulation.

It is thus understood that continuous phase is understood as meaning a distribution such that all or the majority of the internal parts of the active principle are only separated from the surface by active principle or a mixture of active principle and a substance not opposing the diffusion or the dissolution of the active principle.

Advantageously, the mixture formed by the active principle and the excipient is homogeneous at all points.

The delayed-release formulations according to the invention are additionally characterized by their difference of duration of release in vitro and in vivo.

Thus, the formulations according to the invention placed in a physiological aqueous medium release the active principle over a period of less than seven days although the duration of action in vivo is substantially greater than this period, advantageously one month at least, and preferably at least three months.

The matrix formulations comprising the same quantity of active principle conversely had a longer release in vitro, of the same order of size as the duration of release in vivo.

Surprisingly, despite an in vitro release of a limited duration, the formulations according to the invention allow a considerably greater duration of release to be obtained in vivo without relation to the duration of release in vitro.

In addition, the release profile in vivo is clearly different from that of the two-phase matrix forms and will be of pseudo order 0, corresponding to a constant diffusion of the active principle in the course of time.

This release profile constitutes another advantage since it allows a liberation of active principle of a constant level in the body.

The formulations according to the invention are injected directly in their solid form in the absence of any liquid excipient; the high proportion of active principle thus constitutes a determining advantage, by allowing the volume to be reduced significantly.

Thus, with respect to a matrix form with 20% of active principle, the novel formulations according to the invention with, for example, 70% of active principle allow the volume to be reduced by a factor of 3.5 or even the dose to be multiplied by 3.5 for an identical volume.

This signifies that where, for a given active principle with a non-dispersed matrix formulation, a trocar was necessary to inject an implant of a diameter of greater than 1.8 mm, a standard intramuscular needle suffices to deposit a microimplant of a formulation according to the invention having a diameter of less than 1 mm.

In addition, the method of release of the formulation of the invention, without absorption of fluids, nor initial swelling of a matrix, constitutes a stability advantage for the active principle which is preserved in a controlled environment. The delayed-release forms according to the invention are thus particularly advantageous for fragile active principles such as recombinant proteins.

To the extent where no limitation exists for the active principle taking account of the nature of the biodegradable biocompatible polymer forming the excipient, it is possible to incorporate into the formulations according to the invention active principles of high molecular weight which were not capable of diffusing in the matrix forms of the prior art, especially synthetic or natural macromolecules, especially proteins, or their analogues.

The invention thus allows liberation over a sustained period of fragile molecules, especially peptides and proteins, or their analogues.

Among the active substances which can be used for the invention, it is especially possible to mention proteins, peptides chosen, for example, in the group formed of Triptoreline acetate, lanreotide acetate, of a compound having an LH-RH activity such as Triptoreline, goserelin, leuprorelin, buserelin or their salts, an LH-RH antagonist, a GPIIb/IIIa antagonist, a compound having an activity similar to a GPIIb/IIIa antagonist, erythropoietin (EPO) or one of its analogues, the different a interferons, interferon β or γ, somatostatin, a derivative of somatostatin such as described in the European patent EP 215171 whose contents are incorporated by reference, an analogue of somatostatin such as described in the American patent U.S. Pat. No. 5,552,520 (this patent itself contains a list of other patents describing analogues of somatostatin which are incorporated by reference in the present application), insulin, a growth hormone, a growth hormone release factor (GRF), an epidermal growth factor (EGF), a melanocyte-stimulating hormone (MSH), a thyrotropin release hormone (TRH) or one of its salts or derivatives, a thyroid-stimulating hormone (TSH), a luteinizing hormone (LH), a follicle-stimulating hormone (FSH), a parathyroid hormone (PTH) or one of its derivatives, a hydrochloride of lysozyme, a peptide fragment at the N-terminal end (position 1→34) of human PTH hormone, vasopressin or one of its derivatives, oxytocin, calcitonin, a derivative of calcitonin having an activity similar to that of calcitonin, glucagon, gastrin, secretin, pancreozymin, cholecystokinin, angiotensin, human placenta lactogen, human chorionic gonadotropin (HCG), enkephalin, colony-stimulating factor, an enkephalin derivative, endorphin, kyotorphin, the interleukins, for example interleukin 2, tuftsin, thymopoietin, thymosthymine, thymic humoral factor (THF), thymic serum factor (TSF), a derivative of thymic serum factor (TSF), thymosin, thymic factor X, tumour necrosis factor (TNF), motilin, bombesin or one of its derivatives such as described in the American patent U.S. Pat. No. 5,552,520 (this patent itself contains a list of other patents describing derivatives of bombesin which are incorporated by reference in the present application), prolactin, neurotensin, dynorphin, caerulein, substance P, urokinase, asparaginase, bradykinin, kallikrein, nerve growth factor, a blood coagulation factor, polymixin B, colistin, gramicin, bacitracin, a peptide stimulating protein synthesis, an antagonist of endothelin or one of its salts or derivatives, a vaso-active intestinal polypeptide (VIP), adrenocorticotropic hormone (ACTH), a platelet-derived growth factor (PDGF), a bone morphogenetic protein (BMP), and a gastric inhibitor polypeptide. (GIP). Any other water-soluble active substance, or one of its salts or precursors, will likewise be able to be used by the persons skilled in the art if he judges it useful.

Preferably, a water-soluble product obtained by salification in cation form will be used, with, for example, acetic acid. However, it is possible to use an insoluble salt, such as the pamoate.

Peptide and/or protein are/is understood as meaning as well as the peptide and/or the protein themselves, pharmacologically active fragments of these peptides or proteins.

The water-soluble active substance such as used to manufacture the formulations or implants according to the invention can in particular be Triptoreline acetate, lanreotide acetate, goserelin, leuprorelin, buserelin or their salts.

These formulations additionally have the advantage of being able to be administered with the aid of the use of the above device for the process according to the invention.

The manufacturing processes of formulations according to the invention depend on mixing techniques, compression techniques, techniques of extrusion in the molten state and grinding techniques, conventionally used in the field of the manufacture of delayed-release pharmaceutical forms.

The invention likewise relates to a process for preparation of a delayed-release formulation according to the invention having the steps consisting in:
  producing a homogeneous mixture of the active principle and of the excipient, containing at least 50% of active principle;
  compacting the said mixture; and
  extruding the said compacted mixture in the molten state.

An alternative process applying generally to the matrix and non-matrix compositions, whatever the content of active principle and of excipient, especially of PLGA, and intended for local as well as for non-local application and necessitating neither solvent, nor heating of the mixture, comprises the steps consisting in:
  producing a homogeneous mixture of the active principle and of the excipient;
  subjecting the homogeneous mixture to high compression, preferably with a force of greater than 1000 kg;
  grinding the compressed articles obtained; and
  putting into a form suitable for administration.

According to the first process, the process is carried out, for example, in the following manner:

The active principle (AP) and the PLGA are weighed in the proportions by weight of the mixture (for example 70% AP and 30% PLGA).

Mixing is carried out to obtain a homogeneous mixture, for example with the aid of a ®Turbula mixer. The mixture is then loaded into a compression die.

A compaction is carried out which corresponds, in fact, to a "gentle" compression which allows briquettes to be formed of, for example, 13 mm diameter by 5 mm thickness. This is advantageously carried out with a knuckle-joint press.

The briquettes are pulverized, which can be carried out, for example, by screening, cryopulverization with balls or with a knife mill.

The object of this operation is to improve the quality of the powder mixture flow during the extrusion necessary in this particular situation where the molten parts represents less than 50% of the total.

The mixture is extruded through a die of the same diameter as the desired microimplants. The extrudate is recovered after control of the diameter by laser beams (Keyence) on a light drawing tractor.

Preferentially, the microimplants are calibrated by the extrusion nozzle and not by drawing.

The extrudate is cut to the desired length as a function of the analytical control to obtain the microimplants which are then loaded into the injection devices before gamma-irradiation (25 kGy).

According to the second process, the process is carried out, for example, as follows:

Starting from a mixture of AP and PLGA, the process is no longer a simple compaction but a very high compression of the mixture starting with the same constituents (excipients and active principle).

It will be possible to obtain this hypercompression with a minimum force of one ton.

The consequence of this hypercompression carried out at a significant diameter, for example 13 mm or greater, is the transformation of this thermoplastic excipient (capable of melting at temperature) into a structure similar to that obtained under hot conditions, that is to say transparent or vitreous, very different from the former obtained after simple compaction.

This operation takes place at ambient temperature, in cold conditions or even below 0° C. During this hypercompression, at a low temperature, the vitreous transition to the plastic state of the excipient within the mixture is obtained.

It will be possible to recompact these hypercompressed articles then pulverized as above in the form of micro-compressed articles equivalent to the preceding microimplants.

This technique particularly suited to the delayed-release forms of PLGA allows without temperature, or solvent, or manufacturing vehicles, the obtainment of pharmaceutical forms which are of particular interest for preserving the integrity of the active principle, especially for fragile molecules such as, for example, recombinant proteins.

This process is likewise of interest for the manufacture of matrix forms (not comprising more than 50% of active principle) whether these are dispersed or non-dispersed. For the matrix forms, the compression of the PLGA leads to a matrix structure equivalent to that obtained by making the excipient melt on heating.

The hyper-compressed articles after pulverization can be used directly in a dispersed microparticles form.

It will be possible to inject the dispersed form directly after loading into a needle of a device such as that described above or to inject it in suspension in a liquid medium (such as for the microspheres, for example).

One of the possible aspects for the solid form is that of an elongated cylinder.

The formulation such as defined above can, preferably, have the forms and dimensions defined above in relation to the described local administration device.

Advantageously, the formulation is in the form of a cylinder of diameter less than 3 mm, preferably less than 1 mm and of length less than 50 mm, preferably less than 30 mm, the total volume being less than 50 mm$^3$, preferably 20 mm$^3$.

The invention likewise relates to a method of therapeutic treatment comprising injection into a patient necessitating a treatment involving the liberation of an active principle of a formulation according to the invention over a sustained period.

The formulation can be advantageously injected by the subcutaneous or intramuscular route.

This can be carried out by any suitable means, especially a standard injection needle having a diameter of less than 1 mm.

The invention likewise relates to the use of a solid formulation such as defined above for the obtainment of a delayed-release effect.

The examples below illustrate the invention:

EXAMPLE 1

Intrasinusoid Insert of Dexamethasone Phosphate, PLGA Form

The manufacture of the inserts of dexamethasone phosphate take place according to the following phases:

weighing of the raw materials, mixing, first extrusion, grinding and screening, dosage and packaging, all under class A laminar flow in a class D clean room, and finally sterilization.

For a batch, it will be possible, for example, to weigh 38.25 g of PLGA lactide-coglycolide copolymer (50:50) and to incorporate 6.75 g of disodium dexamethasone-21-phosphate pulverized to less than 100 micrometres.

The powder will be mixed with the aid of the three-dimensional movement mixer and on the first extrusion, the quality of the mixture will be controlled (% of AP).

After extrusion, the mixture is pulverized and extruded again in canes of diameter 2 to 2.5 whose homogeneity is verified (% AP, AP content/length). The weight of the insert necessary for obtaining a dose equivalent to 7.5 mg of dexamethasone phosphate is thus calculated. The cylinders are cut to lengths corresponding to the necessary weight and they are packaged individually in the containing devices which will be gamma-irradiated (25 kGy).

It will be possible to use the device directly inside a trocar of diameter 3 mm and length 10 cm according to the diagrams of FIGS. 5 to 10.

Before testing the efficacy of these inserts, for example in chronic nasal occlusion, on the maxillary sinus, the in-vitro and in-vivo release are verified on a model capable of being predictive of the life of the insert.

Figure 18:
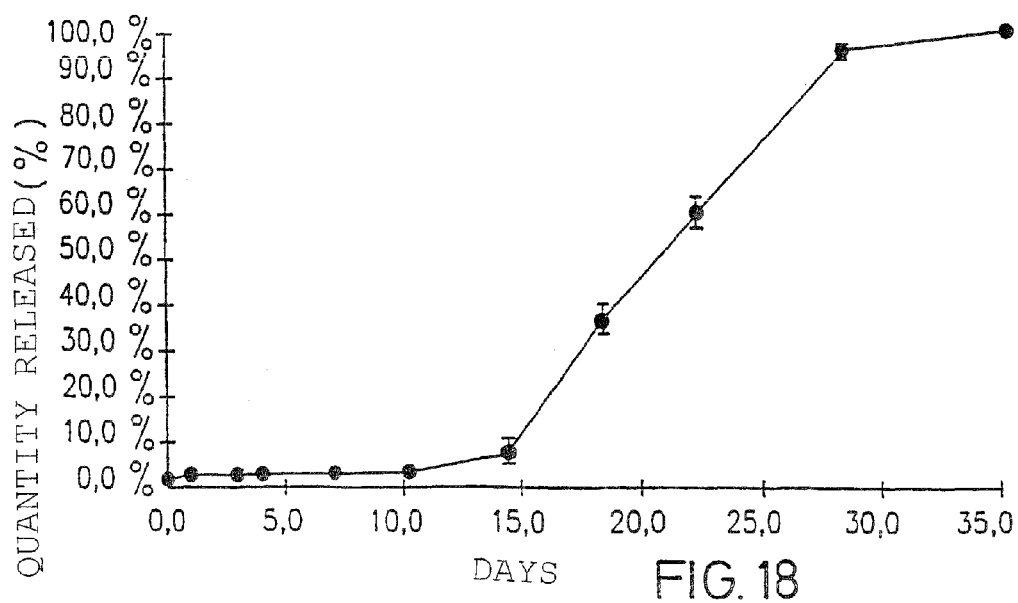
Figure 19:
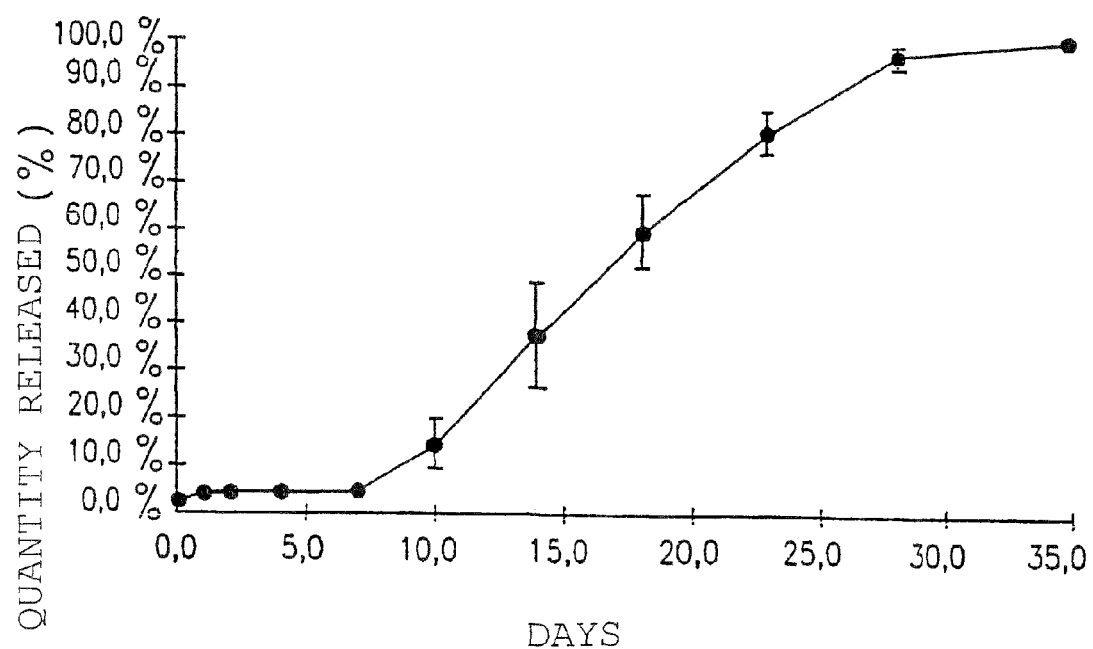

In vitro, the release is followed by determination of the AP by HPLC in an isotonic medium inside which the insert is immersed. FIGS. 17, 18 and 19 show these in-vitro releases for three different concentrations of AP of 10, 15 and 20% respectively.

In vivo, a rat model is used. The insert is administered either subcutaneously or intraperitoneally and the release is evaluated over a month to the nearest decimal point by determining the quantity of AP remaining in the insert after sacrifice of the animals and sampling at determined times.

Figure 20A:
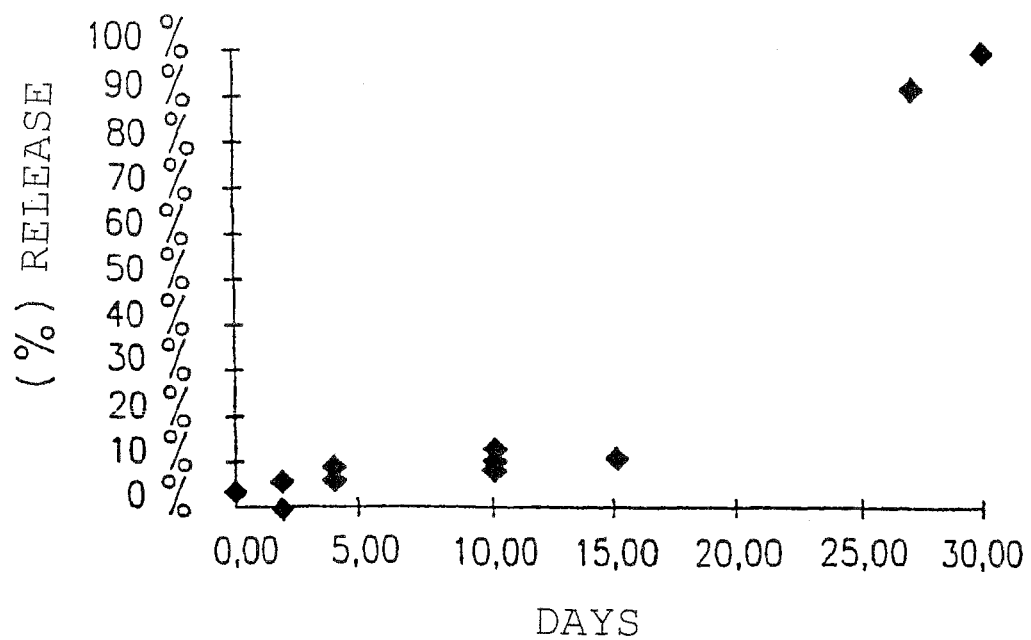
FIGS. 20, 21 and 22 show the results of pharmacokinetic studies on rats of inserts of dexamethasone at a respective concentration of 10, 15 and 20% injected subcutaneously (A) and intra-peritoneally (B).
Figure 20B:
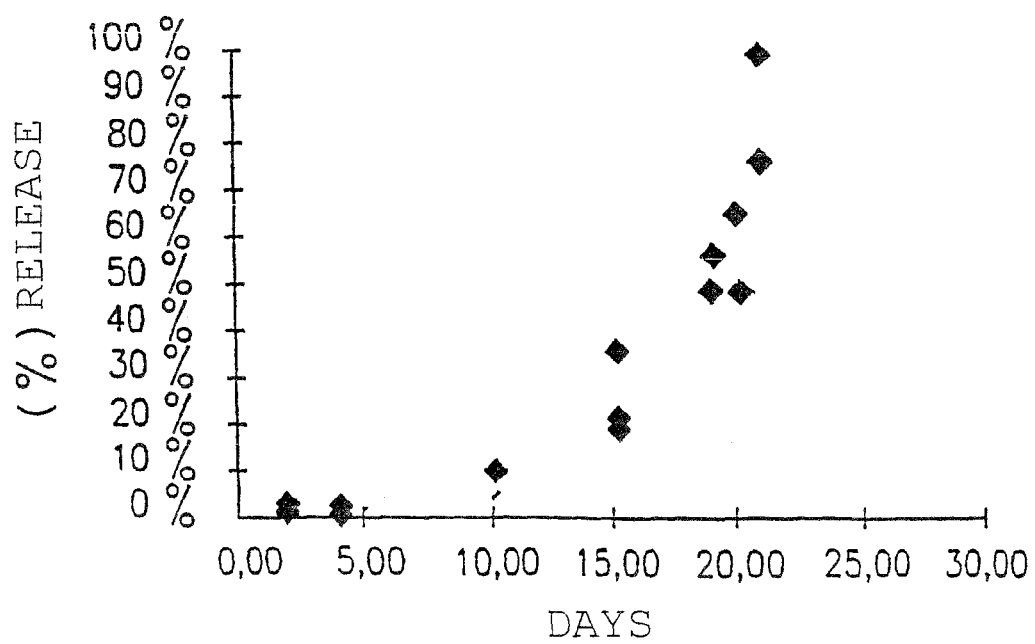
Figure 21A:
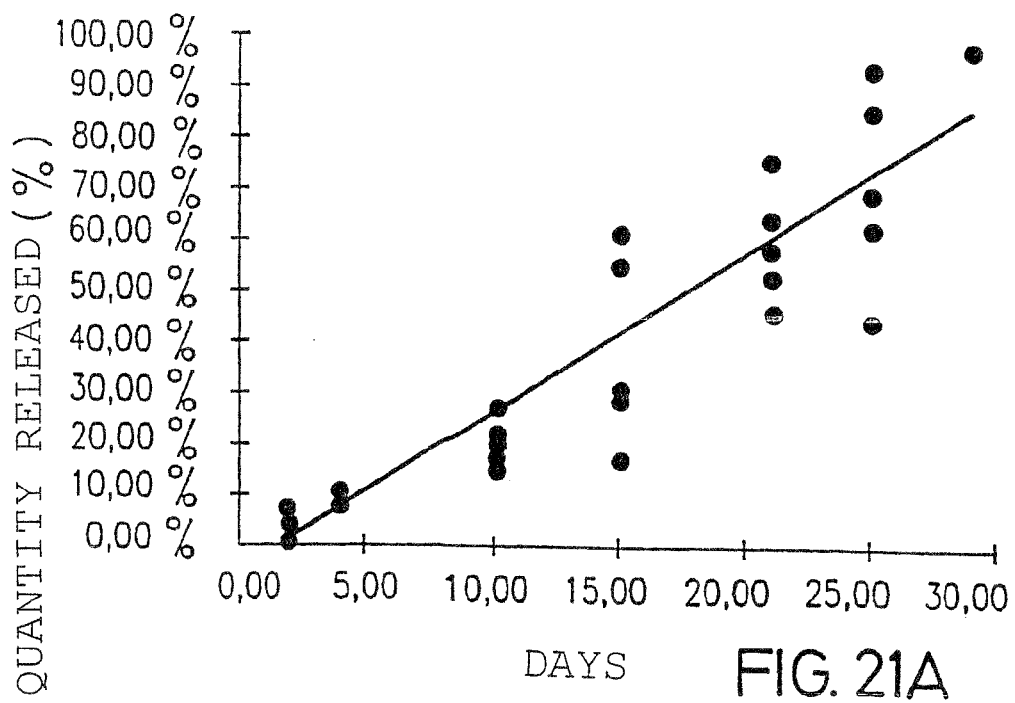
Figure 21B:
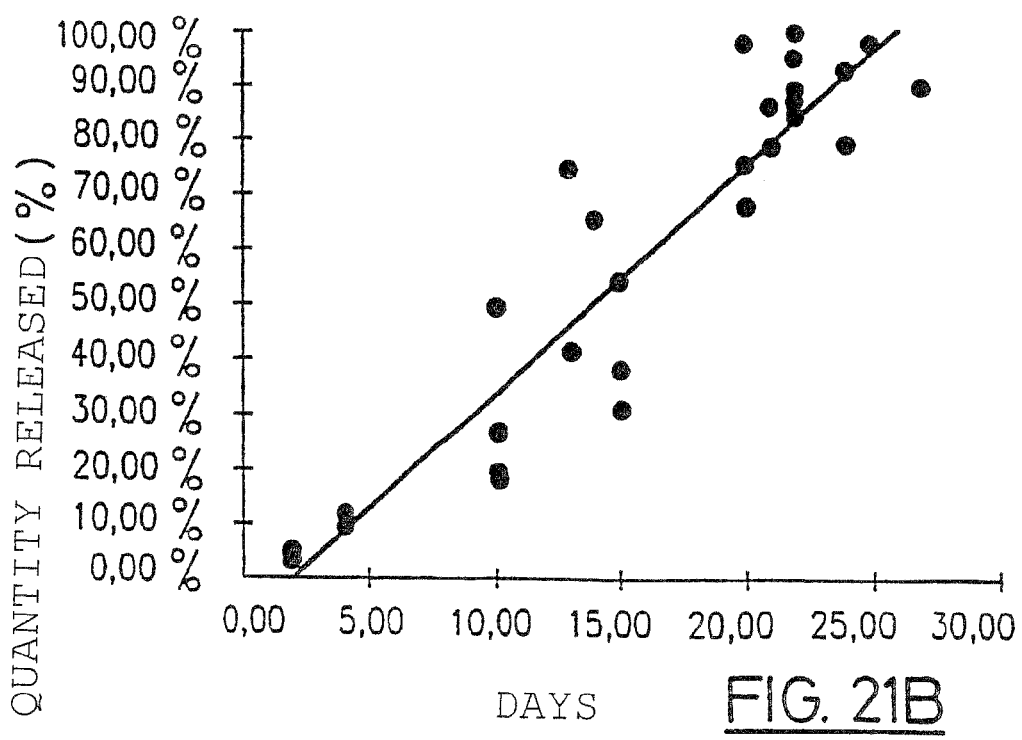
Figure 22A:
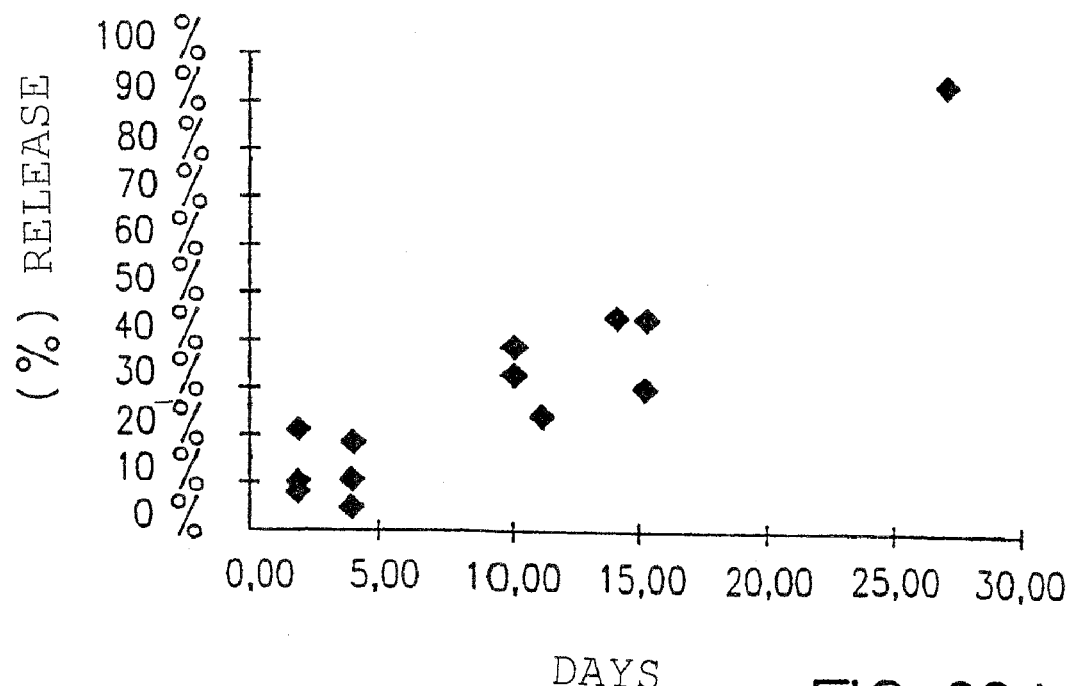
Figure 22B:
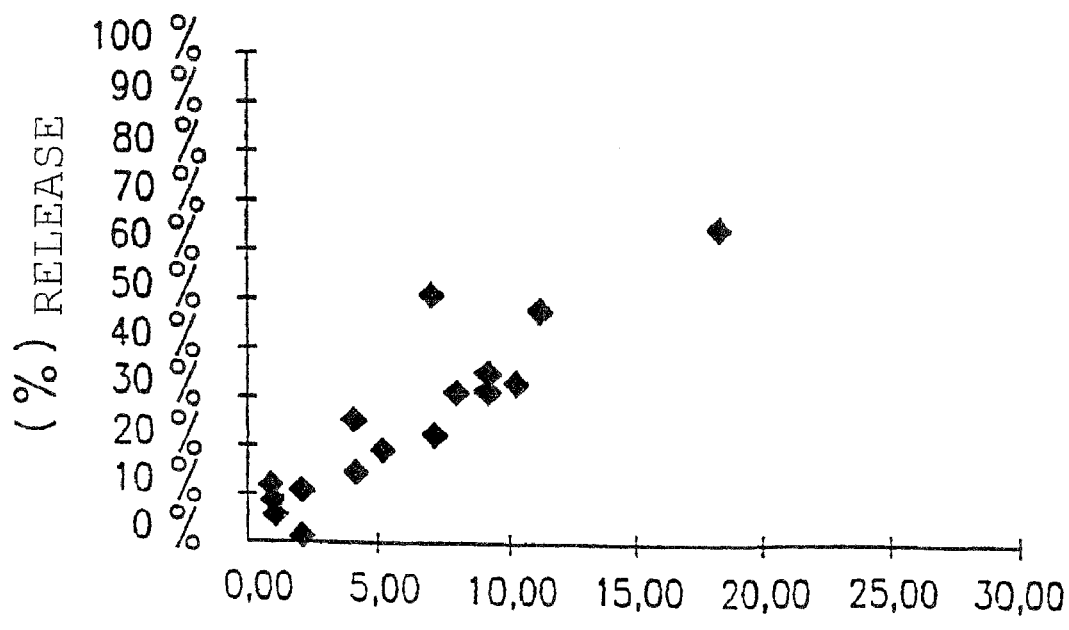

FIGS. 20, 21 and 22 show the results of this in-vivo control at three percentages subcutaneously (A) and intraperitoneally (B).

EXAMPLE 2

Transluminal Implant of Lanreotide Acetate, Solid Form

Implants or cylinders of diameter 0.75 mm and length 30 mm were manufactured. They contain 12.80 mg of lanreotide (BIM23014C) for a composition with 90% of lanreotide acetate and 10% of mannitol.

For a batch size of 200 units or 4.5 g of solid (lanreotide acetate/mannitol), the manufacture comprises the following steps: weighing, connection, evacuation, hydration, mixing, extrusion, drying, arrangement and irradiation.

Weighing corresponds to the volume of the water/mannitol solution, on the one hand, in a syringe and to the somatulin acetate powder in the other syringe.

Connection is the combination of the two syringes via a 3-way ball valve.

Evacuation is then carried out inside the AP powder.

Hydration is obtained by contacting the powder under vacuum with the mannitol solution. Mixing is carried out by to and fro movements by operating the pistons of the two syringes. After checking the HPLC homogeneity, extrusion corresponds to the production of a cane through a die suited to the desired diameter.

This extrusion is likewise obtained by operating the piston of the syringe with a motor.

Drying is carried out after or before the cutting of the cylinders. It consists in evaporating the water from the pasty mixture to obtain the dry cylinder.

Arrangement consists in introducing the cylinder inside the injection needle in a device of diameter 1 mm such as is shown in FIG. 5.

Irradiation by sterilization, after packaging of the device, is carried out with 25 kGy.

It will be possible to inject this device at the local level to deposit the cylinder of lanreotide before or after angioplasty, like a stent, through the lumen of the catheter.

The local delayed-release effect of this formulation has previously been evaluated intra-muscularly (i.m.) on dogs, and i.m. and subcutaneously (s.c.) in man.

Figure 23:
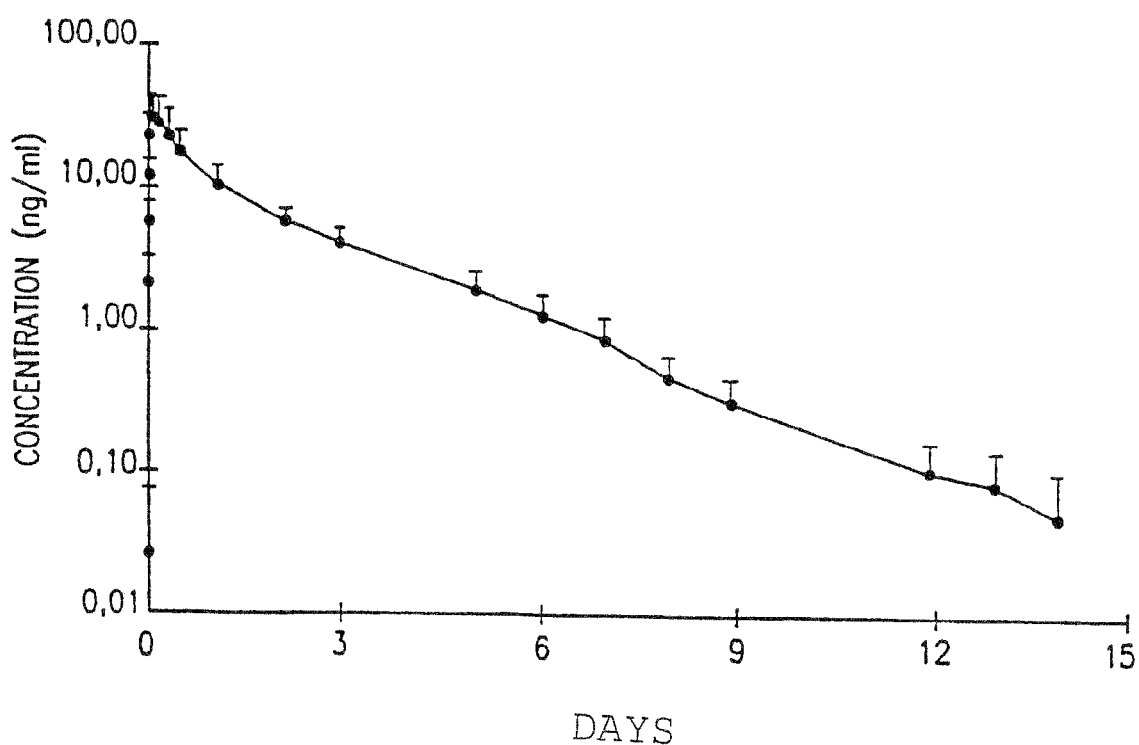
FIGS. 23 and 24 show results of pharmacokinetic studies of the solid form 12.8 mg of lanreotide acetate respectively on the dog injected intra-muscularly and on the healthy volunteer injected subcutaneously (A) and intramuscularly (B).

FIG. 23 shows the result of pharmacokinetics on dogs of the 12.8 mg solid form of lanreotide intramuscularly.

Figure 24A:
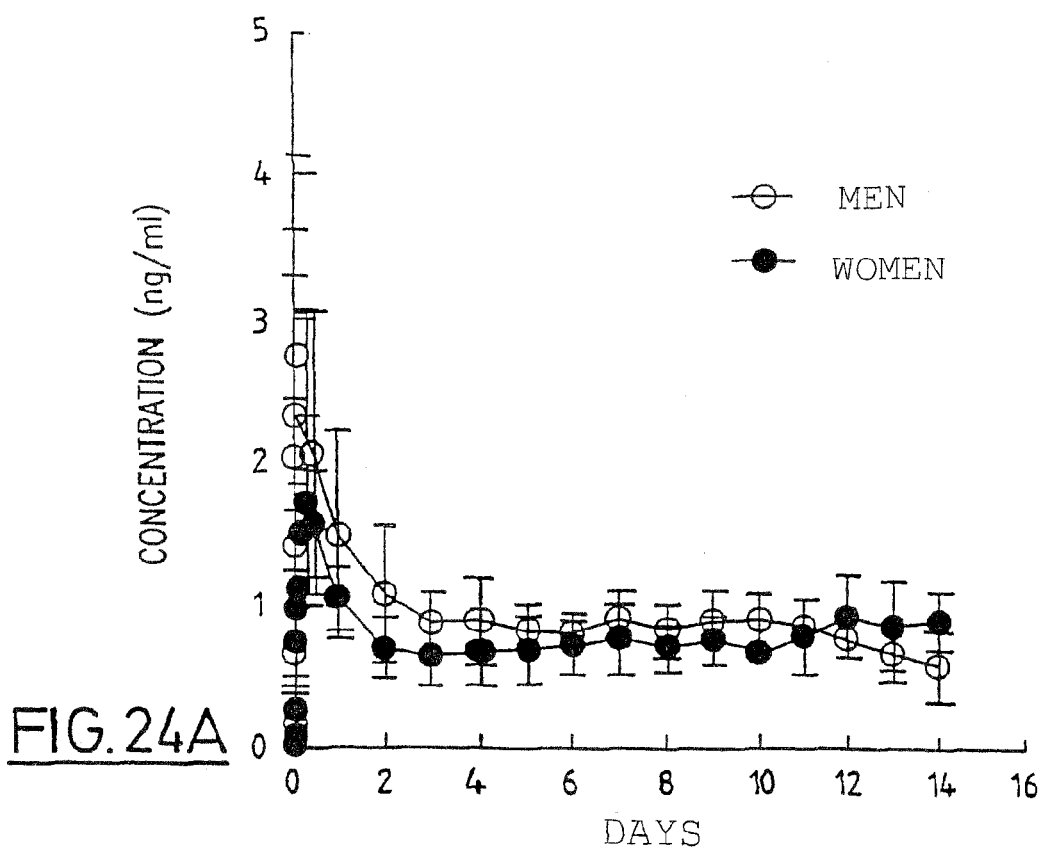
Figure 24B:
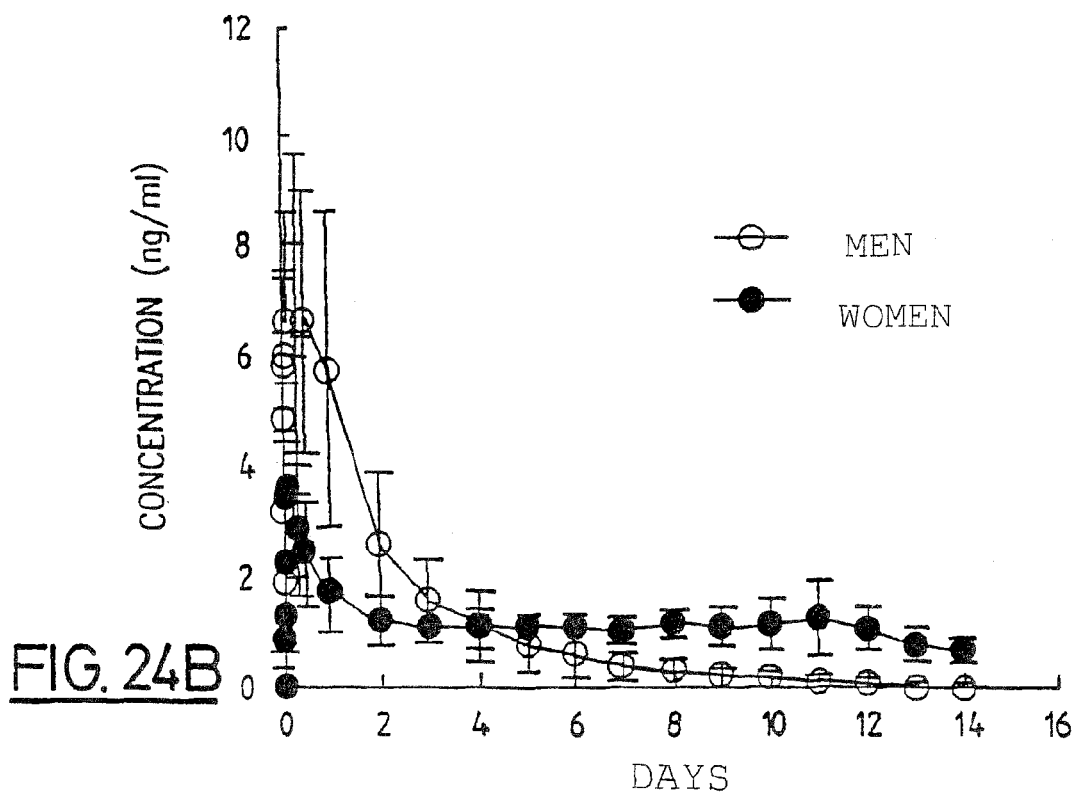

FIG. 24 shows the results of kinetics in healthy volunteers subcutaneously (A) and intra-muscularly (B).

The results obtained allow a sustained delayed-release effect to be considered at the local level of angioplasty with a high local concentration over this period.

EXAMPLE 3

Semi-Solid Depot of Lanreotide Acetate

Lanreotide acetate forms an injectable delayed-release paste or a semi-solid with water.

The delayed-release effect is obtained by deposition, directly from the active principle. This delayed-release effect is modulable as a function of the percentage. The duration of action is thus directly proportional to the erosion or elimination of this semi-solid depot. It is thus possible to combine any other active principle, for which the combined local effect will be sought, with lanreotide. It will be possible to evaluate the duration of action of the AP(s) by the pharmacokinetics of the lanreotide alone.

The semi-solid is manufactured according to a process close to that of the solid of Example 2 without mannitol. Extrusion, drying and rearrangement are replaced by distribution. For example, for 200 units 40 g of lanreotide acetate will be prepared in the case of the 35% lanreotide acetate, 65% water one-month form and for injected doses of 40 mg of AP.

The manufacturing steps are weighing, connection, evacuation, hydration, mixing, distribution and irradiation.

Figure 25:
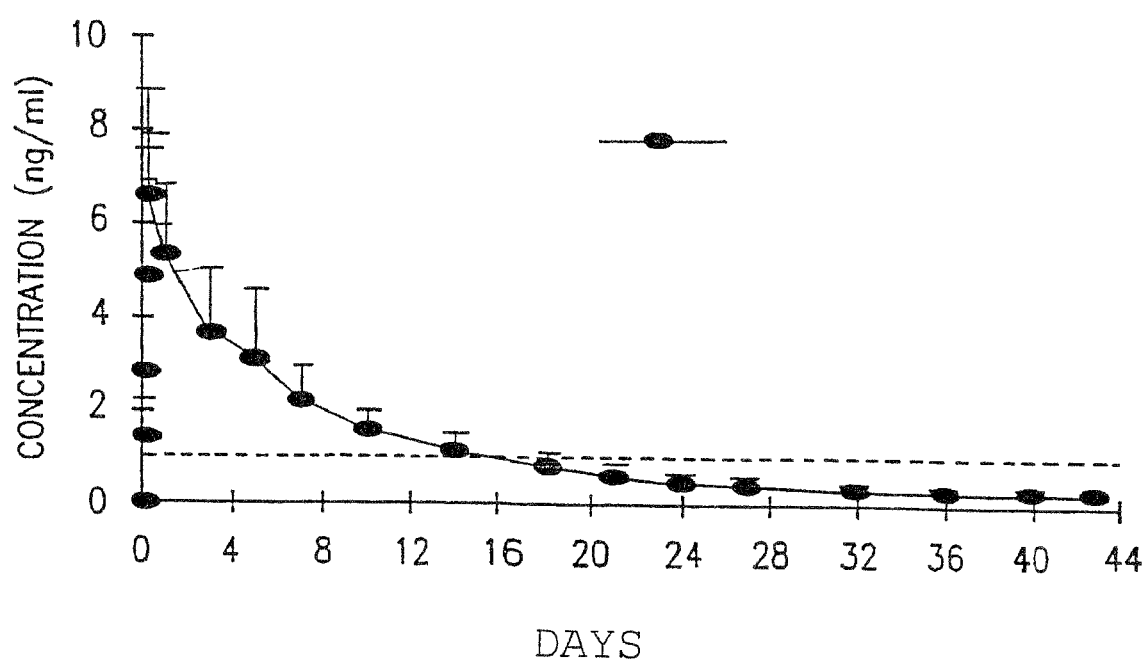
FIG. 25 shows the pharmacokinetic study on. healthy volunteers of the semi-solid form of 40 mg of lanreotide injected intramuscularly.

Distribution consists in a volumetric filling of the injection device (FIGS. 11 to 16), for example, by rotary piston from the mixture syringe. This semi-solid formulation has been the subject of a clinical trial in healthy volunteers intramuscularly (FIG. 25).

It will thus be possible to then obtain a form which is local over one month. The concentration and the quantity of paste will determine the duration and the intensity of the local diffusion.

EXAMPLE 4

Comparison of a 20% Matrix form of Active Principle with a 52% Non-Matrix Form

A very soluble Triptoreline acetate (TA) salt is mixed with a PLGA (75:25) of molecular weight more than 100,000 and of inherent viscosity equal to 1 dl/g in chloroform which only undergoes hydrolysis by loss of mass capable of controlling a matrix liberation after one month.

20% (before percolation) and 52% by weight mixtures of active principle in PLGA are thus prepared. These mixtures are extruded so as to form implants whose release is verified in vitro at 37° C. in 10 ml of physiological serum and without stirring.

Figure 26:
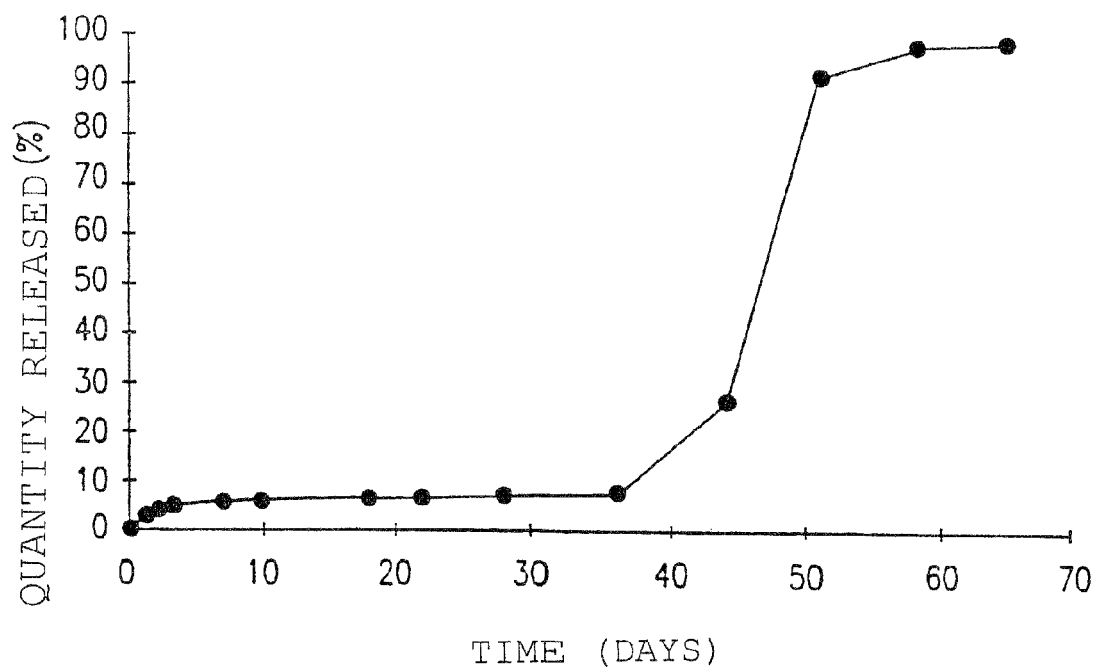
FIG. 26 shows the in vitro release profile of a Triptoreline acetate/PLGA (75:25) matrix formulation with 20% of active principle.
Figure 27:
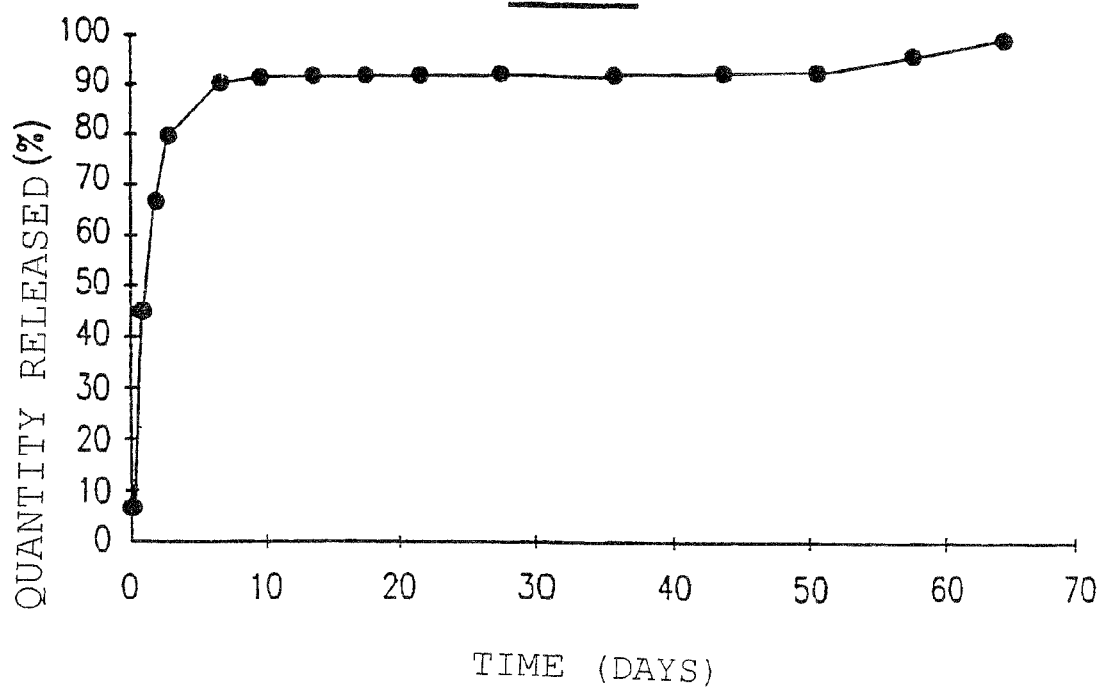
FIG. 27 shows the in vitro release profile of a Triptoreline acetate/PLGA (75:25) formulation according to the invention with 52% of active principle.

The 20% implants of active principle only liberate 4% of the total dose in two days and only 6.7% in 36 days before the loss of mass of the polymer takes place which involves the liberation of the active principle between d36 and d60 (FIG. 26) The 52% implants of active principle liberate 66% of the total dose in two days and more than 90% in one week (FIG. 27).

EXAMPLE 5

Comparison of a Matrix and Non-Matrix Form with an Insoluble Salt of Triptoreline (Triptoreline Pamoate)

Two formulations of Triptoreline pamoate and PLGA (50:50) are prepared, the first with 40% and the second with 52% of active principle.

The liberation of these two formulations is compared in an in-vitro release model (the low solubility of the active principles necessitates a suspending volume of 100 ml).

Figure 28:
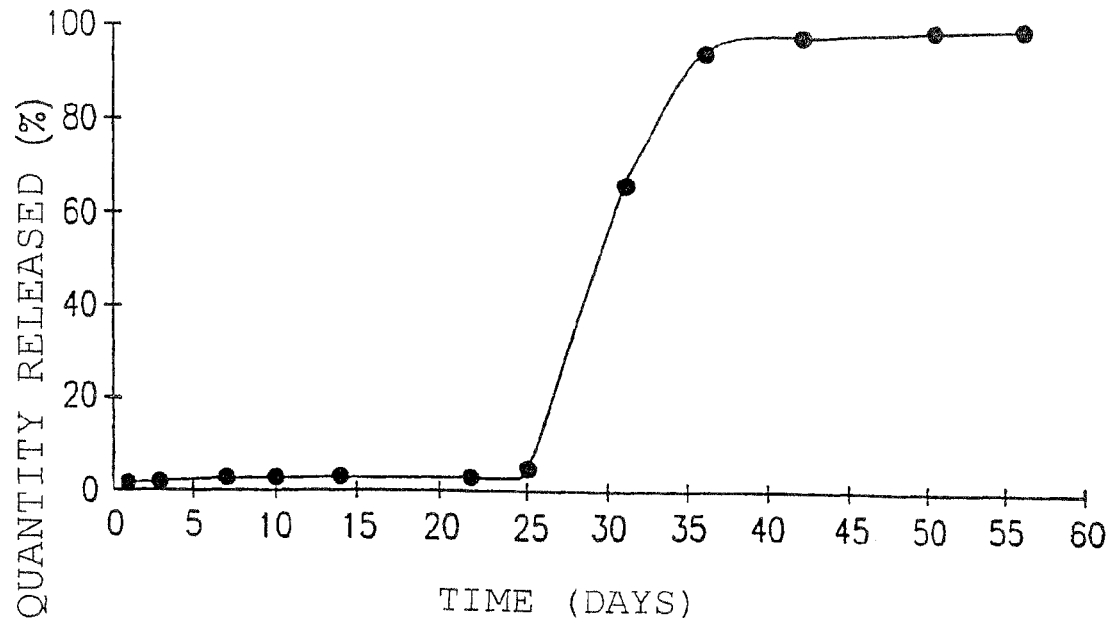
FIG. 28 shows the in vitro release profile of a Triptorelin pamoate (active principle) and PLGA (50:50) formulation with 40% of active principle.
Figure 29:
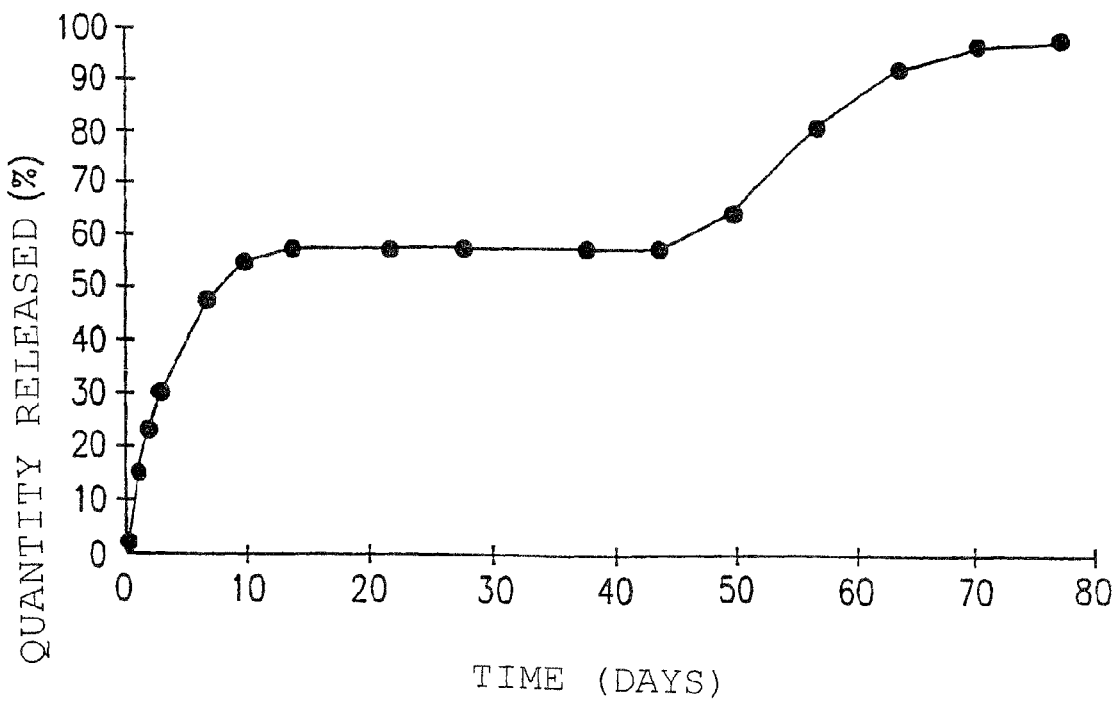
FIG. 29 shows the in vitro release profile of a Triptoreline pamoate (active principle) and PLGA (50:50) formulation with 52% of active principle.

Despite the insolubility of the active principle, a matrix-type release with 40% is observed (FIG. 28). At 52% (FIG. 29), the release is already essentially independent of the matrix.

The in-vitro functioning of the active principle with respect to the PLGA in matrix and non-matrix mode thus does not depend on the solubility of its salt.

EXAMPLE 6

Macroscopic Difference in Mode of Action between Matrix Formulation and Non-Matrix Form The matrix preparation of Example 4, 75:25 PLGA/Triptoreline acetate (80%-20%) in a non-disperse form after ten days in a physiological medium in vitro contains virtually all its active principle; it has a translucent appearance with an increase in diameter and a decrease in length with respect to time 0 (FIG. 30), which demonstrates a constraint of the PLGA matrix.

The 75:25 PLGA/Triptoreline acetate (48%-52%) non-matrix preparation under the same conditions after ten days is virtually totally devoid of active principle. It has not undergone a change in diameter or in length (FIG. 31).

The active principle has thus escaped from the PLGA non-matrix skeleton. In this case, the active principle is free of any physicochemical constraint with the polymer. The PLGA remains unchanged in the course of the release of the active principle.

EXAMPLE 7

Figure 32:
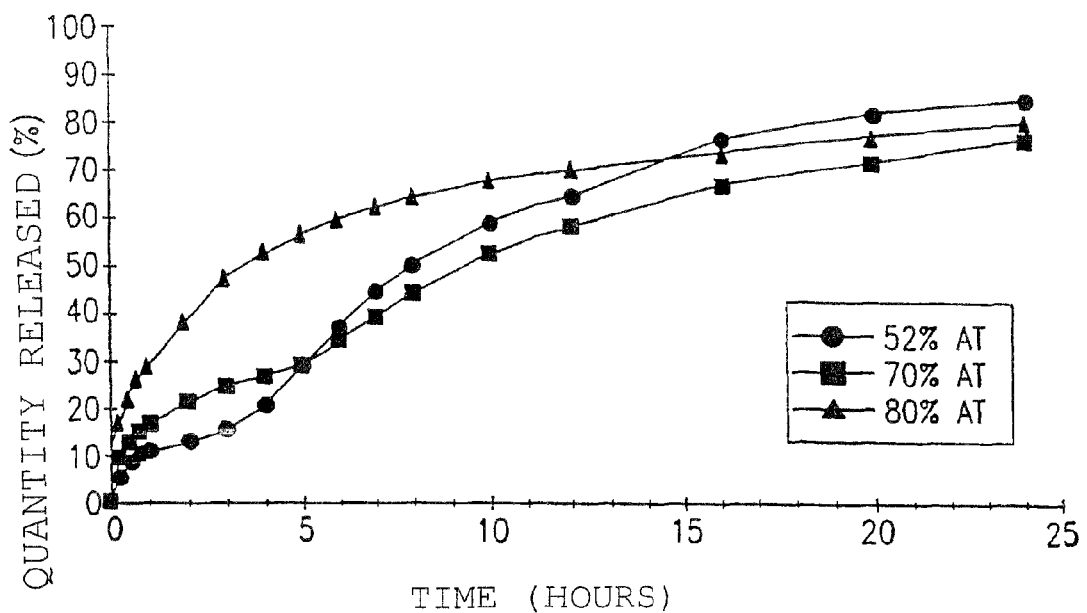
FIG. 32 shows the in vitro release profiles of three forms according to the invention with 52%, 70% and 80% of active principle (Triptoreline acetate) at a dose of 9 mg.

Comparison between Non-Matrix Form (52% of Triptoreline Acetate) and Non-Matrix Forms with 70% and 80% of Triptoreline Acetate In the same in-vitro release model as in Example 4, three non-matrix forms were compared at the same dose of 9 mg. The release results over one day (FIG. 32) demonstrate a similarity of action of these three formulations. The release value obtained in vitro is thus not proportional to the C.L. This demonstrates the role of the active principle and of its total quantity in the action of the non-matrix forms.

EXAMPLE 8

Figure 33:
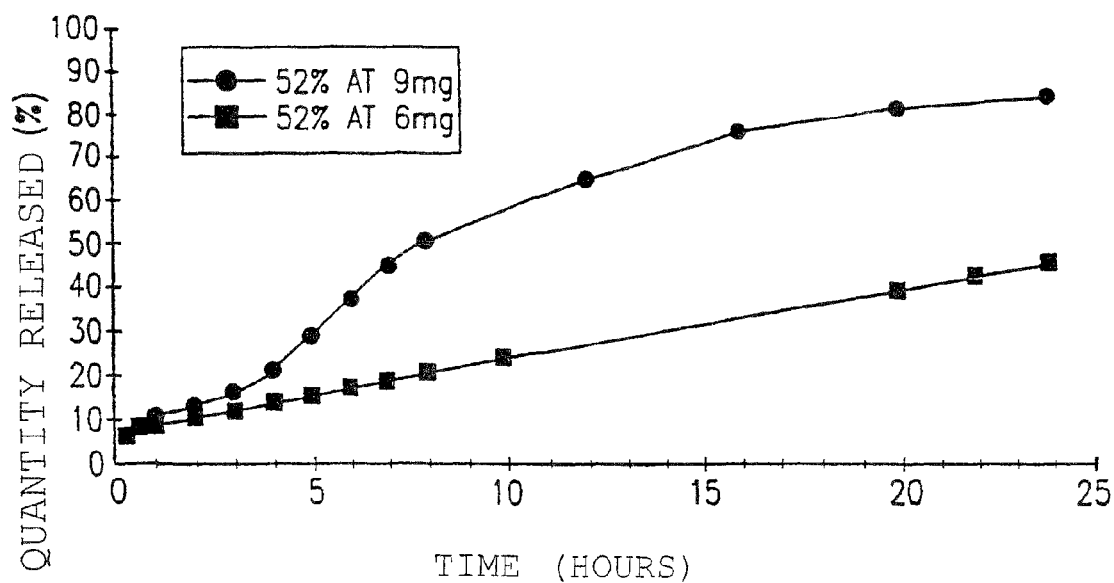
FIG. 33 shows the in vitro release profiles of two forms according to the invention with 52% of active principle (Triptoreline acetate) at doses of 9 mg and 6 mg.

Comparison of the In-Vitro Liberation of the 52% Non-Matrix Forms in a Dose of 6 mg and 9 mg Two formulations using the same 75:25 PLGA of MW greater than 100,000 were produced with a C.L. of 52% of Triptoreline acetate (TA). These two formulations were checked in vitro, the first at a dose of 9 mg (52% of TA in 9 mg) and the second at a dose of 6 mg (52% of TA in 6 mg). The results (FIG. 33) demonstrate a difference in release kinetics linked to the difference in dose of active principle.

EXAMPLE 9

Comparison of Matrix Forms with 52%, 70% and 80% of Active Principle (Triptoreline Acetate) in an In-Vivo Trial in Rats Two batches of implants with 52% of active principle, one batch of implant with 70% of active principle and one batch of implant with 80% of active principle were injected subcutaneously in four groups of 12 rats: 4 animals from each group were sacrificed on d1, d4 and d19. The implants were recovered and determined by HPLC in order to know the residual quantities of active principle.

Figure 34:
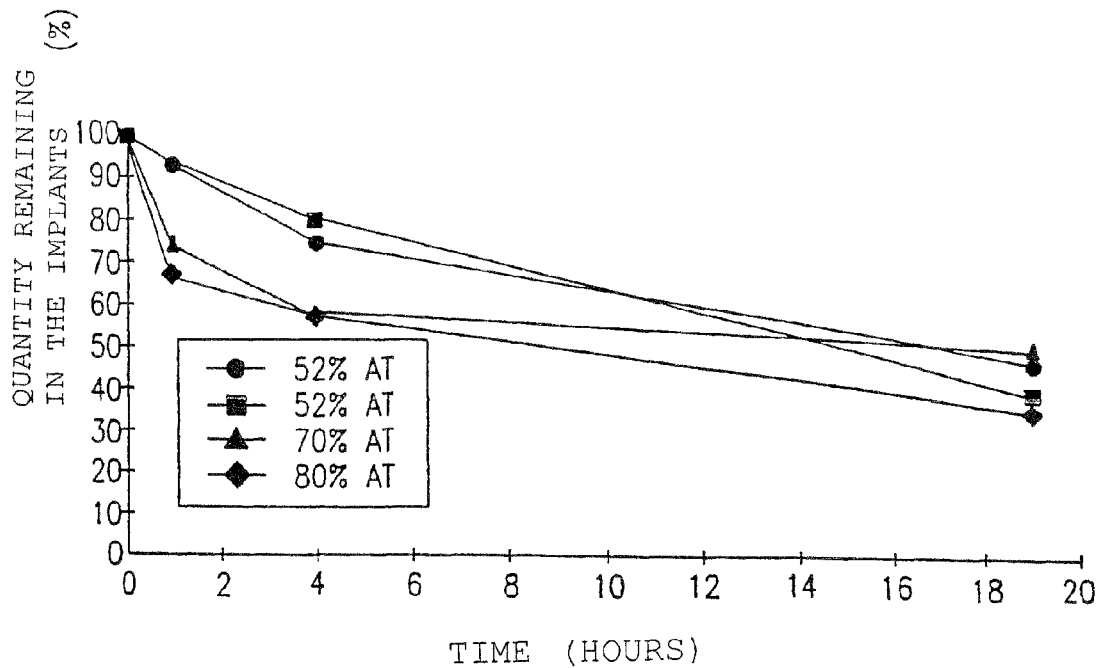
FIG. 34 shows the development in the course of time of amounts of active principle remaining in implants injected into rats for formulations with 52%, 70% and 80% of active principle (Triptoreline acetate).

The results of FIG. 34 express the residual level of the implants as a percentage between d0 and d19.

An obvious parallelism is noted in the decrease of this percentage between the 52%, 70% or 80% forms.

Figure 35:
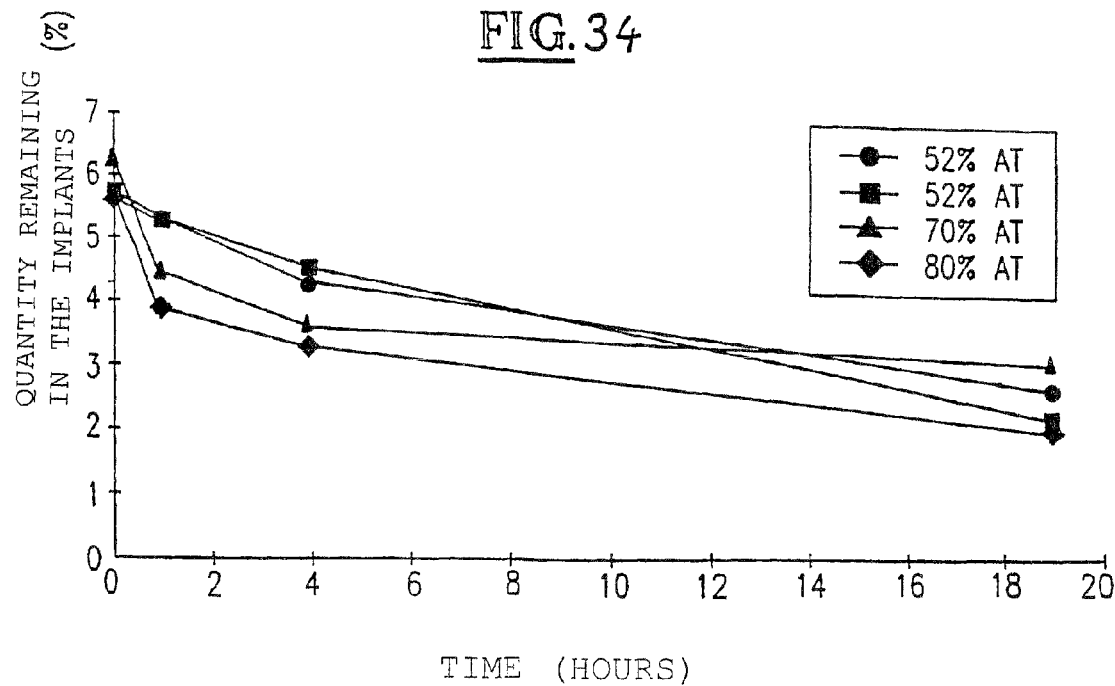
FIG. 35 shows the development in the course of time of the absolute residual quantity of active principle remaining in implants injected into rats for formulations with 52%, 70% and 80% of active principle (Triptoreline acetate).

FIG. 35 represents the development of the residual quantity of pure active principle in mg. It is noted that contrary to the results in vitro after 19 days, on average there remains a quantity of active principle which is significant and equivalent in the 52% implants and in the 70% and 80% implants.

Plasma samples were taken on these animals before sacrifice and this result was confirmed by an RIA analysis.

EXAMPLE 10

Figure 36:
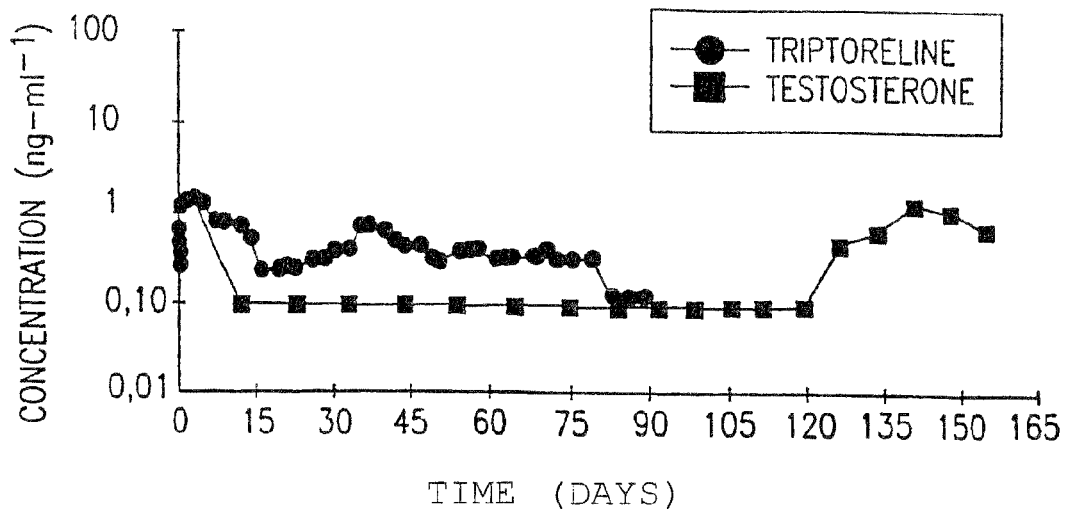
FIG. 36 shows the kinetics in dogs of plasma concentrations for a Triptoreline acetate/PLGA (75:25) formulation with 20% of active principle and at a dose of 3 mg and the monitoring of the pharmaceutical effect by the level of testosterone.
Figure 37:
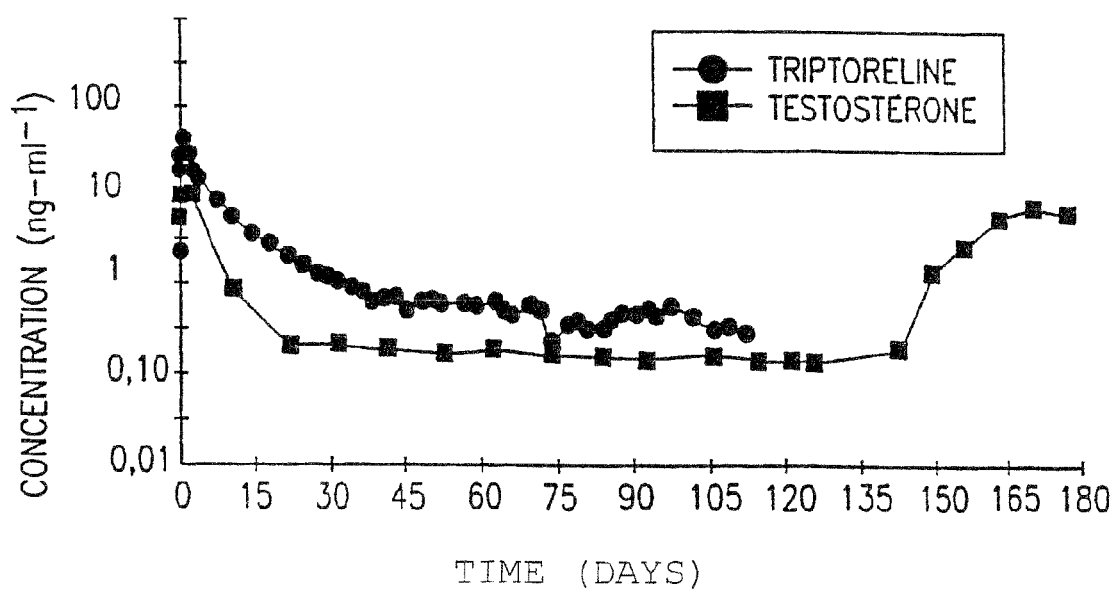
FIG. 37 shows the kinetics in dogs of plasma concentrations for a Triptoreline acetate/PLGA (75:25) formulation with 52% of active principle and at a dose of 6 mg and the monitoring of the pharmaceutical effect by the level of testosterone.

Pharmacokinetic Result of a Matrix Formulation (20% of Active Principle) and of a Non-Matrix Formulation (52% of Active Principle) in Dogs The 20% and 52% formulations of Triptoreline acetate were injected i.m. into two series of six dogs in respective total doses of 3 and 6 mg of pure Triptoreline and the kinetics were followed by RIA analysis of the plasma samples as well as the dynamic efficacy of the active principle with the testosterone levels (FIGS. 36 and 37).

The results demonstrate a release activity over three months at least in the two cases.

The kinetics of the 20% form show a conventional profile (with peak and rebound). The kinetics of the 52%. form are not comparable to those of the conventional PLGA forms but are of pseudo 0 order without peak or rebound.

EXAMPLE 11

Pharmacokinetic Results of a Non-Matrix Formulation with 70% of Active Principle in Dogs A formulation using the same PLGA and the same active principle as the 52% formulation of active principle (Example 10) was produced with 70% and 30% of PLGA.

Figure 38A:
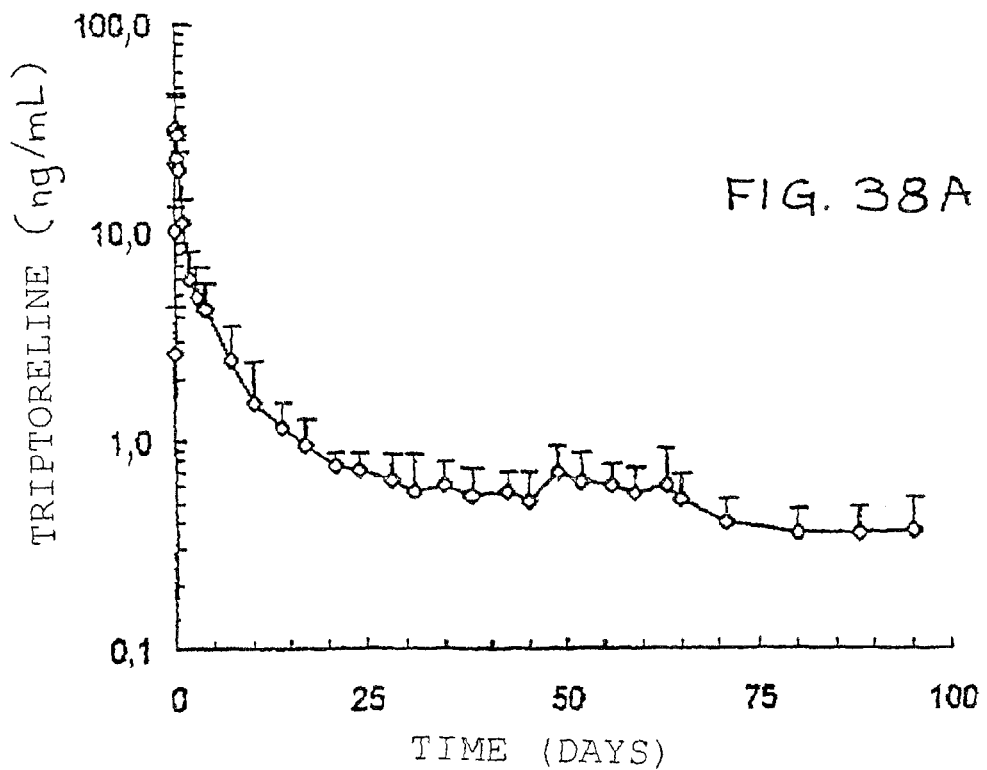
FIG. 38 shows the in vivo release profiles in dogs of a Triptoreline acetate/PLGA (75:25) formulation with 70% of active principle and at a dose of 9 mg (A) and the monitoring of the pharmaceutical effect by the amount of testosterone (B).
Figure 38B:
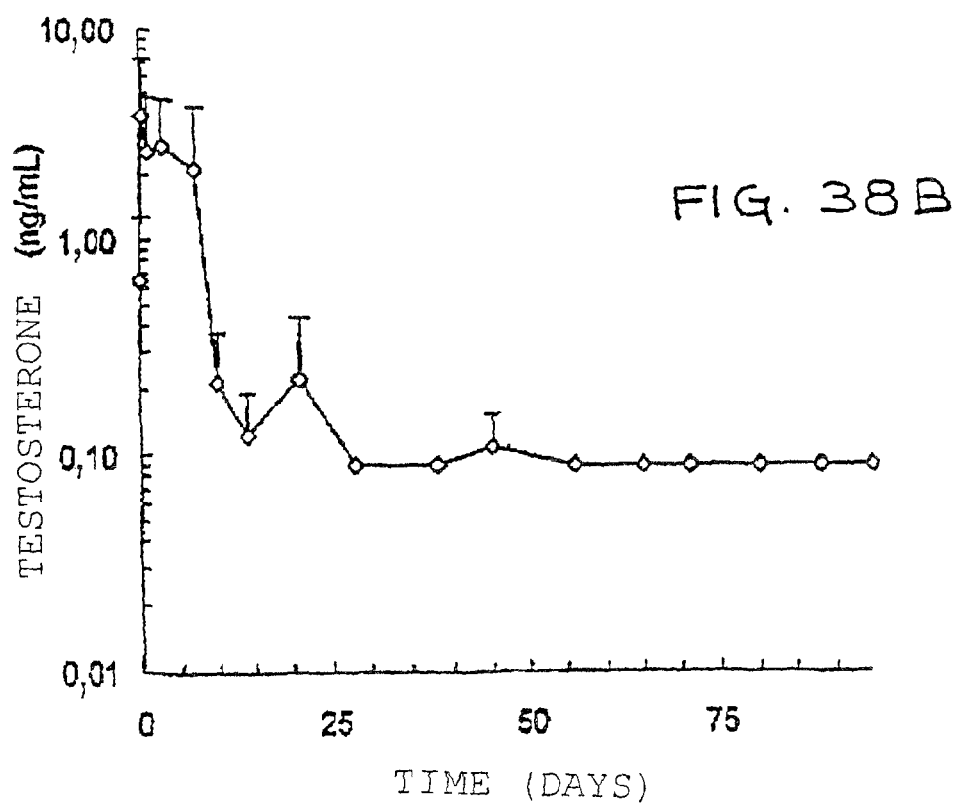

This formulation was injected i.m. in the dog at a total dose of 9 mg of pure Triptoreline. The kinetics were followed by RIA analysis of plasma samples (FIG. 38A) as well as the dynamic efficacy of the active principle with testosterone levels (FIG. 38B).

The results indeed show a release activity over at least three months as for the 52% form of active principle with, as the only difference, a higher release level on making the total dose vary.

Figure 39:
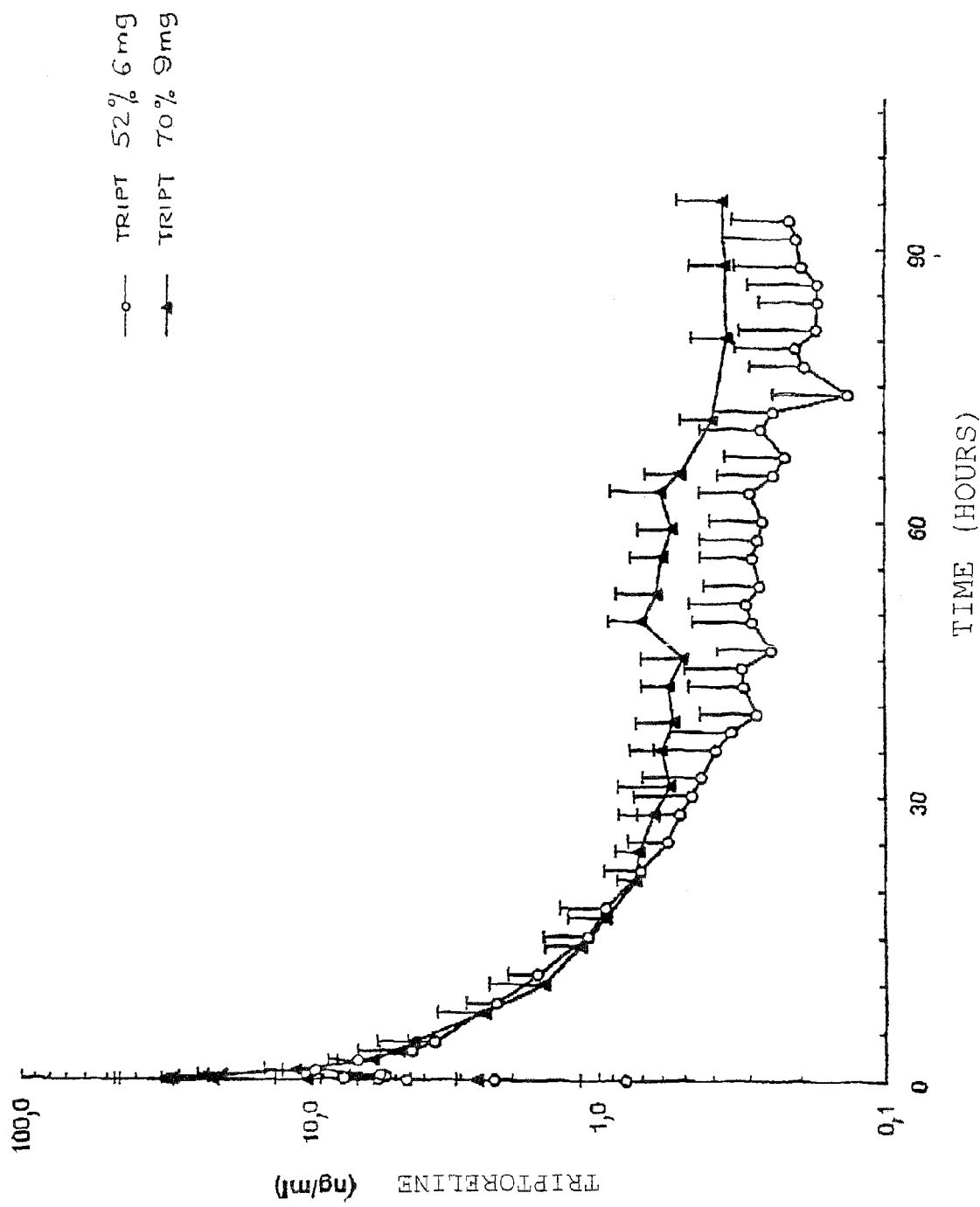
FIG. 39 shows the in vivo release profiles in dogs of a Triptoreline acetate/PLGA formulation with 52% of active principle and at a dose of 6 mg and with 70% of active principle and at a dose of 9 mg.

The variation of the loading between 52% and 70% does not influence either the duration or the profile and the release level indeed depends on the total dose injected (FIG. 39).

The invention claimed is:

1. An assembly for implantation and insertion of a solid or semi-solid formulation into a precise depot site of a patient's body such that the formulation is able to persist for a certain period in the site, the assembly comprising:
    a solid or semi-solid formulation containing at least one active principle;
    an administration device containing the solid or semi-solid formulation; and
    an invasive device configured for placement inside of the body to reach the depot site and sized to receive the administration device,
    wherein the administration device has a thin and elongated form, and comprises a tubular guide with a piston extending through the guide, a first part for placement inside of the body and a second part for remaining outside of the body during use,
    the administration device is configured to be positioned inside of and operated by the invasive device,
    the first part is configured to (i) package the solid or semi-solid formulation into a desired shape for implantation or inserting, (ii) position the formulation at the depot site, (iii) inject or insert the formulation at the depot site, and (iv) be withdrawn after insertion or injection, and
    the second part is configured to operate the administration device.

2. The assembly according to claim 1, wherein the invasive device is a trocar.

3. The assembly according to claim 1, wherein the invasive device is a catheter.

4. The assembly according to claim 1, wherein the invasive device is an endoscope.

5. The assembly according to claim 1, wherein the invasive device is an instrument adapted for a surgical route of approach.

6. The assembly according to claim 1, wherein the formulation is a delayed-release formulation.

7. The assembly according to claim 1, wherein the formulation contains a low dose of active principle with respect to a customary dose, for a treatment by systemic route, of the active principle considered.

8. The assembly according to claim 1, wherein the formulation has a cylindrical form.

9. The assembly according to claim 8, wherein the formulation has a diameter of between 0.1 to 3 mm.

10. The assembly according to claim 9, wherein the formulation has a minimum length/diameter ratio of 10:1.

11. The assembly according to claim 1, wherein the formulation is solid, and is deformable by being preconstrained in the administration device to regain an original shape in situ.

12. The assembly according to claim 1, wherein the first part being configured to package the formulation preconstrains the formulation in the administration device and the formulation regains a non-rectilinear shape once placed in the depot site.

13. The assembly according to claim 1, wherein a length and a diameter of the formulation are selected to avoid its elimination or its displacement.

14. The assembly according to claim 1, wherein the at least one active principle of the formulation is releasable in secretions of a mucous membrane in a cavity.

15. The assembly according to claim 14, wherein the cavity or mucous membrane is of a facial or otorhinolaryngology (ORL) sphere.

16. The assembly according to claim 14, wherein the mucous membrane is a tracheopulmonary mucous membrane.

17. The assembly according to claim 14, wherein the mucous membrane is the buco-oesophageal mucous membrane.

18. The assembly according to claim 14, wherein the at least one active principle of the formulation is transportable by mucus.

19. The assembly according to claim 1, wherein the formulation comprises a corticoid.

20. The assembly according to claim 1, wherein the formulation contains an anti-inflammatory active principle.

21. The assembly according to claim 1, wherein the formulation contains a concentration of active principle of between 20 and 100%.

22. The assembly according to claim 21, wherein the formulation has a concentration of active principle of between 40 and 100%.

23. The assembly according to claim 22, wherein the formulation has a concentration of active principle of between 50 and 100%.

24. The assembly according to claim 1, wherein the active principle is combined with a polylactide-glycolide (PLGA) copolymer excipient.

25. The assembly according to claim 1, wherein the formulation contains an active principle of one of a peptide and a protein.

26. The assembly according to claim 1, wherein,
the formulation is a delayed-release formulation, which comprises the at least one active principle and a biodegradable excipient,
the excipient is a polylactide-glycolide (PLGA) copolymer, and
the concentration of active principle is between 40 and 100%.

27. The assembly according to claim 26, wherein the concentration of active principle is between 50 and 100%.

28. The assembly according to claim 26, wherein the formulation has a cylindrical form with a diameter not exceeding 3 mm.

29. The assembly according to claim 28, wherein the formulation has a diameter not exceeding 2 mm.

30. The assembly according to claim 28, wherein the formulation has a diameter of the order of 0.1 mm.

31. The assembly according to claim 28, wherein the formulation has a minimum length to diameter ratio of 10.

32. The assembly according to claim 26, wherein,
the delayed-release formulation is a solid formulation for parenteral administration, which comprises a homogeneous mixture of an active principle in a non-dispersed state forming a continuous phase of which at least one part is in direct contact with an exchange surface of the formulation and of an exterior biological medium, and of a biodegradable biocompatible excipient in which the quantity of active principle is at least 50% by weight with respect to the total weight of the formulation, and
the formulation has a release profile independent of the excipient, molecular weight of the excipient, or of ratio of the weight of the active principle to the weight of excipient, and
the release profile is dependent on the total quantity of active principle in the formulation.

33. The assembly according to claim 32, wherein the biodegradable biocompatible excipient is a polymer or copolymer of lactic and/or glycolic acid or a mixture of polymers and/or copolymers of lactic and/or glycolic acid.

34. The assembly according to claim 33, wherein the said biodegradable biocompatible polymer is a copolymer of lactic acid and glycolic acid (PLGA).

35. The assembly according to claim 32, wherein the said biodegradable biocompatible polymer is a copolymer of lactic acid and glycolic acid having an intrinsic viscosity in chloroform at 1 g per 100 ml of greater than 0.6 dl/g.

36. The assembly according to claim 34, wherein the copolymer of lactic acid and glycolic acid is of hydrophilic nature.

37. The assembly according to claim 32, wherein,
the formulation placed in vitro in a physiological liquid medium release almost all of the active principle in less than a week, and
the formulation placed in vivo subcutaneously or intramuscularly releases the active principle over a period substantially greater than one week.

38. The assembly according to claim 32, wherein the formulation comprises a mixture of the active principle and the excipient which is homogeneous at all points.

39. The assembly according to claim 32, wherein the release takes place in a single diffusion phase of the active principle.

40. The assembly according to claim 32, wherein,
the active principle is at least 51% by weight with respect to the total weight of the formulation, and
the excipient is less than 50% by weight with respect to the total weight of the formulation.

41. The assembly according to claim 32, wherein, the active principle is one of a peptide and a protein.

42. The assembly according to claim 1, wherein the administration device has a maximum diameter of 3 mm.

43. The assembly according to claim 42, wherein the administration device has a diameter less than 2.5 mm.

44. The assembly according to claim 42, wherein the administration device has a diameter less than 2 mm.

45. The assembly according to claim 1, wherein the formulation comprises an active principle which has local effect.

46. The assembly according to claim 1, wherein the formulation contains dexamethasone with a concentration between 10 and 20%.

47. The assembly according to claim 19, wherein the corticoid is suited to treat a cavity, cavity wall or mucous membrane, of naso-sinusoid polyposis, of allergic or non allergic rhinitis, of types of non-infectious otitis or sinusitis.

48. The assembly according to claim 1, wherein the invasive device has been pre-positioned in the body prior to positioning the administration device inside the invasive device.

* * * * *